United States Patent
Vargas et al.

(10) Patent No.: US 6,371,964 B1
(45) Date of Patent: Apr. 16, 2002

(54) TROCAR FOR USE IN DEPLOYING AN ANASTOMOSIS DEVICE AND METHOD OF PERFORMING ANASTOMOSIS

(75) Inventors: Jaime Vargas, Palo Alto; Brendan M. Donohoe, San Francisco; Scott C. Anderson, Sunnyvale; Theodore Bender, Palo Alto; Stephen Yencho, Menlo Park; Bernard Hausen, Menlo Park; Michael Hendricksen, Menlo Park, all of CA (US)

(73) Assignee: Vascular Innovations, Inc., Menlo Park, CA (US)

( * ) Notice: Subject to any disclaimer, the term of this patent is extended or adjusted under 35 U.S.C. 154(b) by 0 days.

(21) Appl. No.: 09/440,263

(22) Filed: Nov. 15, 1999

Related U.S. Application Data

(63) Continuation-in-part of application No. 09/314,278, filed on May 18, 1999.

(51) Int. Cl.$^7$ ............................................. A61B 17/04
(52) U.S. Cl. ..................... 606/153; 606/181; 606/184
(58) Field of Search ........................... 606/152–155, 606/158, 181, 184

(56) References Cited

U.S. PATENT DOCUMENTS

| | | |
|---|---|---|
| 3,254,650 A | 6/1966 | Collito |
| 3,519,187 A | 7/1970 | Kapitanov et al. |
| 3,774,615 A | 11/1973 | Lim et al. |
| 4,214,587 A | 7/1980 | Sakura, Jr. |
| 4,350,160 A | 9/1982 | Kolesov et al. |
| 4,352,358 A | 10/1982 | Angelchik |
| 4,366,819 A | 1/1983 | Kaster |
| 4,368,736 A | 1/1983 | Kaster |
| 4,503,568 A | 3/1985 | Madras |
| 4,523,592 A | 6/1985 | Daniel |
| 4,553,542 A | 11/1985 | Schenck et al. |
| 4,589,416 A | 5/1986 | Green |
| 4,593,693 A | 6/1986 | Schenck |
| 4,603,693 A | 8/1986 | Conta et al. |
| 4,607,637 A | 8/1986 | Berggren et al. |

(List continued on next page.)

FOREIGN PATENT DOCUMENTS

| | | |
|---|---|---|
| DE | 29713335.7 | 11/1997 |
| EP | 0 701 800 | 3/1996 |
| EP | 0 885 595 | 12/1998 |
| EP | 99/08603 | 2/1999 |
| EP | 0 938 870 | 9/1999 |
| EP | 0 820 724 | 1/2000 |
| EP | 0 820 725 | 1/2000 |
| EP | 0 913 125 | 7/2000 |
| EP | 0 990 420 | 12/2000 |
| WO | WO92/08513 | 5/1992 |
| WO | 517252 | 12/1992 |
| WO | 96-25886 | 8/1996 |
| WO | 97/25002 | 7/1997 |
| WO | 97/27898 | 8/1997 |
| WO | 97/31575 | 9/1997 |
| WO | 97/47261 | 12/1997 |
| WO | 98/07399 | 2/1998 |
| WO | 98/19608 | 5/1998 |
| WO | WO98/19618 | 5/1998 |
| WO | 98/19625 | 5/1998 |

(List continued on next page.)

*Primary Examiner*—Gary Jackson
(74) *Attorney, Agent, or Firm*—Burns, Doane, Swecker & Mathis, L.L.P.

(57) ABSTRACT

A trocar useful for forming an incision in a target vessel for placement of an anastomosis device which may have an inner flange formed by radial expansion of the device and an outer flange formed by axial compression of the device. The trocar can have a smaller size during formation of the incision and a larger size when retracted over a deployment tool used to deploy the anastomosis device.

29 Claims, 22 Drawing Sheets

U.S. PATENT DOCUMENTS

| | | |
|---|---|---|
| 4,624,255 A | 11/1986 | Schenck et al. |
| 4,624,257 A | 11/1986 | Berggren et al. |
| 4,657,019 A | 4/1987 | Walsh et al. |
| 4,665,906 A | 5/1987 | Jervis |
| 4,747,407 A | 5/1988 | Liu et al. |
| 4,752,024 A | 6/1988 | Green et al. |
| 4,883,453 A | 11/1989 | Berry et al. |
| 4,892,098 A | 1/1990 | Sauer |
| 4,907,591 A | 3/1990 | Vasconcellos et al. |
| 4,917,087 A | 4/1990 | Walsh et al. |
| 4,917,090 A | 4/1990 | Berggren et al. |
| 4,917,091 A | 4/1990 | Berggren et al. |
| 4,930,674 A | 6/1990 | Barak |
| 5,005,749 A | 4/1991 | Aranyi |
| 5,062,842 A | 11/1991 | Tiffany |
| 5,104,025 A | 4/1992 | Main et al. |
| 5,119,983 A | 6/1992 | Green et al. |
| 5,129,913 A | 7/1992 | Ruppert |
| 5,156,613 A | 10/1992 | Sawyer |
| 5,171,262 A | 12/1992 | MacGregor |
| 5,187,796 A | 2/1993 | Wang et al. |
| 5,193,731 A | 3/1993 | Aranyi |
| 5,205,459 A | 4/1993 | Brinkerhoff et al. |
| 5,217,474 A | 6/1993 | Zacca et al. |
| 5,221,281 A | 6/1993 | Klicek .................... 606/45 |
| 5,222,963 A | 6/1993 | Brinkerhoff et al. |
| 5,234,447 A | 8/1993 | Kaster et al. |
| 5,250,058 A | 10/1993 | Miller et al. |
| 5,250,060 A | 10/1993 | Carbo et al. |
| 5,271,544 A | 12/1993 | Fox et al. |
| 5,275,322 A | 1/1994 | Brinkerhoff et al. |
| 5,285,945 A | 2/1994 | Brinkerhoff et al. |
| 5,290,298 A | 3/1994 | Rebuffat et al. |
| 5,292,053 A | 3/1994 | Bilotti et al. |
| 5,304,220 A | 4/1994 | Maginot |
| 5,314,435 A | 5/1994 | Green et al. |
| 5,314,468 A | 5/1994 | Ramos Martinez |
| 5,333,773 A | 8/1994 | Main et al. |
| 5,336,233 A | 8/1994 | Chen |
| 5,350,104 A | 9/1994 | Main et al. |
| 5,354,302 A | 10/1994 | Ko |
| 5,364,389 A | 11/1994 | Anderson |
| 5,366,462 A | 11/1994 | Kaster et al. |
| 5,392,979 A | 2/1995 | Green et al. |
| 5,395,030 A | 3/1995 | Kuramoto et al. |
| 5,395,311 A | 3/1995 | Andrews |
| 5,443,497 A | 8/1995 | Venbrux |
| 5,447,514 A | 9/1995 | Gerry et al. |
| 5,454,825 A | 10/1995 | Van Leeuwen |
| 5,456,712 A | 10/1995 | Maginot |
| 5,456,714 A | 10/1995 | Owen |
| 5,464,449 A | 11/1995 | Ryan et al. |
| 5,465,895 A | 11/1995 | Knodel et al. |
| 5,478,354 A | 12/1995 | Tovey et al. |
| 5,503,835 A | 4/1996 | Sauer et al. |
| 5,515,478 A | 5/1996 | Wang |
| 5,522,834 A | 6/1996 | Fonger et al. |
| 5,524,180 A | 6/1996 | Wang et al. |
| 5,533,661 A | 7/1996 | Main et al. |
| 5,540,677 A | 7/1996 | Sinofsky |
| 5,553,198 A | 9/1996 | Wang et al. |
| 5,556,405 A | 9/1996 | Lary |
| 5,558,667 A | 9/1996 | Yarborough et al. |
| 5,571,167 A | 11/1996 | Maginot |
| 5,643,340 A | 7/1997 | Nunokawa |
| 5,645,520 A | 7/1997 | Nakamura et al. |
| 5,657,429 A | 8/1997 | Wang et al. |
| 5,669,918 A | 9/1997 | Balazs et al. |
| 5,669,934 A | 9/1997 | Sawyer |
| 5,676,670 A | 10/1997 | Kim |
| 5,693,088 A | 12/1997 | Lazarus |
| 5,695,504 A | 12/1997 | Gifford, III et al. |
| 5,702,412 A | 12/1997 | Popov et al. |
| 5,707,362 A | 1/1998 | Yoon |
| 5,707,380 A | 1/1998 | Hinchcliffe et al. |
| 5,709,335 A | 1/1998 | Heck |
| 5,709,693 A | 1/1998 | Taylor |
| 5,725,544 A | 3/1998 | Rygaard |
| 5,725,553 A | 3/1998 | Moenning |
| 5,732,872 A | 3/1998 | Bolduc et al. |
| 5,754,741 A | 5/1998 | Wang et al. |
| 5,762,458 A | 6/1998 | Wang et al. |
| 5,779,718 A | 7/1998 | Green et al. |
| 5,792,135 A | 8/1998 | Madhani et al. |
| 5,797,900 A | 8/1998 | Madhani et al. |
| 5,797,920 A | 8/1998 | Kim |
| 5,799,661 A | 9/1998 | Boyd et al. |
| 5,799,857 A | 9/1998 | Robertson et al. |
| 5,807,377 A | 9/1998 | Madhani et al. |
| 5,814,073 A | 9/1998 | Bonutti |
| 5,815,640 A | 9/1998 | Wang et al. |
| 5,817,113 A | 10/1998 | Gifford, III et al. |
| 5,827,316 A | 10/1998 | Young et al. |
| 5,833,698 A | 11/1998 | Hinchcliffe et al. |
| 5,841,950 A | 11/1998 | Wang et al. |
| 5,855,583 A | 1/1999 | Wang et al. |
| 5,868,763 A | 2/1999 | Spence et al. |
| 5,875,782 A | 3/1999 | Ferrari et al. |
| 5,878,193 A | 3/1999 | Wang et al. |
| 5,879,371 A | 3/1999 | Gardiner et al. |
| 5,881,943 A | 3/1999 | Heck et al. |
| 5,893,369 A | 4/1999 | Lemole |
| 5,904,697 A | 5/1999 | Gifford, III et al. |
| 5,907,664 A | 5/1999 | Wang et al. |
| 5,911,036 A | 6/1999 | Wright et al. |
| 5,915,616 A | 6/1999 | Viola et al. |
| 5,921,995 A | 7/1999 | Kleshinski |
| 5,944,730 A | 8/1999 | Nobles et al. |
| 5,947,363 A | 9/1999 | Bolduc et al. |
| 5,957,363 A | 9/1999 | Heck |
| 5,976,159 A | 11/1999 | Bolduc et al. |
| 6,001,124 A | 12/1999 | Bachinski |
| 6,007,544 A | 12/1999 | Kim |
| 6,013,190 A | 1/2000 | Berg et al. |
| 6,015,416 A | 1/2000 | Stefanchik et al. |
| 6,022,367 A | 2/2000 | Sherts |
| 6,024,748 A | 2/2000 | Manzo et al. |
| 6,030,370 A | 2/2000 | Kupka et al. |
| 6,030,395 A | 2/2000 | Nash et al. |
| 6,036,699 A | 3/2000 | Andreas et al. |
| 6,036,700 A | 3/2000 | Stefanchik et al. |
| 6,036,702 A | 3/2000 | Bachinski et al. |
| 6,036,703 A | 3/2000 | Evans et al. |
| 6,036,704 A | 3/2000 | Yoon |
| 6,036,705 A | 3/2000 | Nash et al. |
| 6,050,472 A | 4/2000 | Shibata |
| 6,053,390 A | 4/2000 | Green et al. |
| 6,056,762 A | 5/2000 | Nash et al. |
| 6,066,144 A | 5/2000 | Wolf et al. |
| 6,066,148 A | 5/2000 | Rygaard |
| 6,068,637 A | 5/2000 | Popov et al. |
| 6,074,416 A | 6/2000 | Berg et al. |
| 6,080,167 A | 6/2000 | Lyell |
| 6,080,173 A | 6/2000 | Williamson, IV et al. |
| 6,083,234 A | 7/2000 | Nicholas et al. |
| 6,110,188 A | 8/2000 | Narciso, Jr. |
| 6,113,612 A | 9/2000 | Swanson et al. |
| 6,117,148 A | 9/2000 | Ravo et al. |
| 6,120,432 A | 9/2000 | Sullivan et al. |
| 6,146,393 A | 11/2000 | Wakabayashi |
| 6,149,681 A | 11/2000 | Houser et al. |

| | | | | | |
|---|---|---|---|---|---|
| 6,152,937 A | 11/2000 | Peterson et al. | WO | 99/62406 | 12/1999 |
| 6,152,945 A | 11/2000 | Bachinski et al. | WO | 99/62409 | 12/1999 |
| 6,165,185 A | 12/2000 | Shennib et al. | WO | 99/62415 | 12/1999 |
| 6,167,889 B1 | 1/2001 | Benetti | WO | WO99/63910 | 12/1999 |
| 6,171,319 B1 | 1/2001 | Nobles et al. | WO | WO99/65409 | 12/1999 |
| 6,171,321 B1 | 1/2001 | Gifford, III et al. | WO | 00/09040 | 2/2000 |
| 6,176,413 B1 | 1/2001 | Heck et al. | WO | 00/10486 | 3/2000 |
| 6,176,864 B1 | 1/2001 | Chapman | WO | 00/12013 | 3/2000 |
| 6,186,942 B1 | 2/2001 | Sullivan et al. | WO | 00/15144 | 3/2000 |
| 6,187,019 B1 | 2/2001 | Stefanchik et al. | WO | 00/15146 | 3/2000 |
| 6,187,020 B1 | 2/2001 | Zegdi et al. | WO | 00/15147 | 3/2000 |
| 6,190,396 B1 | 2/2001 | Whitin et al. | WO | 00/15148 | 3/2000 |
| 6,190,397 B1 | 2/2001 | Spence et al. | WO | 00/15149 | 3/2000 |
| 6,190,590 B1 | 2/2001 | Randall et al. | WO | 00/27310 | 5/2000 |
| 6,193,129 B1 | 2/2001 | Bittner et al. | WO | 00/27311 | 5/2000 |
| 6,193,734 B1 | 2/2001 | Bolduc et al. | WO | 00/27312 | 5/2000 |
| 6,206,912 B1 | 3/2001 | Goldsteen et al. | WO | 00/27313 | 5/2000 |
| 6,206,913 B1 | 3/2001 | Yencho et al. | WO | 00/33745 | 6/2000 |
| 6,235,054 B1 | 5/2001 | Berg et al. | WO | 00/41633 | 7/2000 |

FOREIGN PATENT DOCUMENTS

| | | |
|---|---|---|
| WO | WO98/19629 | 5/1998 |
| WO | 98/19630 | 5/1998 |
| WO | 98/19631 | 5/1998 |
| WO | 98/19632 | 5/1998 |
| WO | WO98/19634 | 5/1998 |
| WO | WO98/19636 | 5/1998 |
| WO | 98/30153 | 7/1998 |
| WO | 98/37814 | 9/1998 |
| WO | WO98/42262 | 10/1998 |
| WO | 98/47430 | 10/1998 |
| WO | 98/55027 | 12/1998 |
| WO | WO99/17665 | 4/1999 |
| WO | 99/18887 | 4/1999 |
| WO | 99/21491 | 5/1999 |
| WO | 99/37218 | 7/1999 |
| WO | WO99/38441 | 8/1999 |
| WO | WO99/38454 | 8/1999 |
| WO | 99/40851 | 8/1999 |
| WO | 99/40868 | 8/1999 |
| WO | WO99/45848 | 9/1999 |
| WO | 99/52481 | 10/1999 |
| WO | 00/53104 | 9/2000 |
| WO | 00/56223 | 9/2000 |
| WO | 00/56226 | 9/2000 |
| WO | 00/56227 | 9/2000 |
| WO | 00/56228 | 9/2000 |
| WO | 00/59380 | 10/2000 |
| WO | 00/66007 | 11/2000 |
| WO | 00/66009 | 11/2000 |
| WO | 00/69343 | 11/2000 |
| WO | 00/69346 | 11/2000 |
| WO | 00/69349 | 11/2000 |
| WO | 00/69364 | 11/2000 |
| WO | 00/72764 | 12/2000 |
| WO | 00/74579 | 12/2000 |
| WO | 00/76405 | 12/2000 |
| WO | 01/08601 | 2/2001 |
| WO | 01/12074 | 2/2001 |
| WO | 01/15607 | 3/2001 |
| WO | 01/17440 | 3/2001 |
| WO | 01/19257 | 3/2001 |
| WO | 01/19259 | 3/2001 |
| WO | 01/19284 | 3/2001 |
| WO | 01/34037 | 5/2001 |

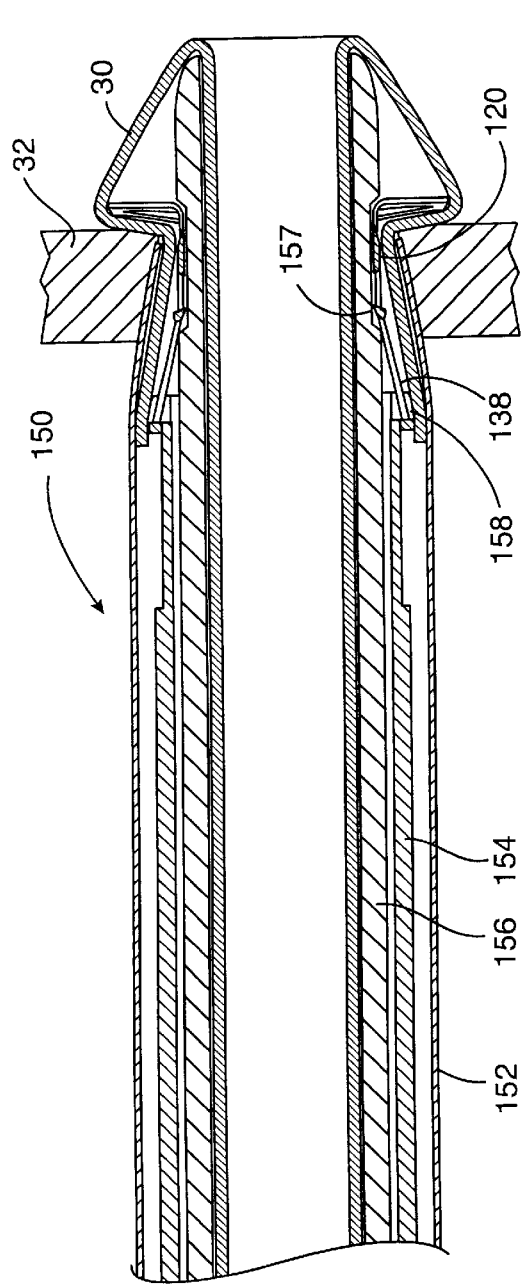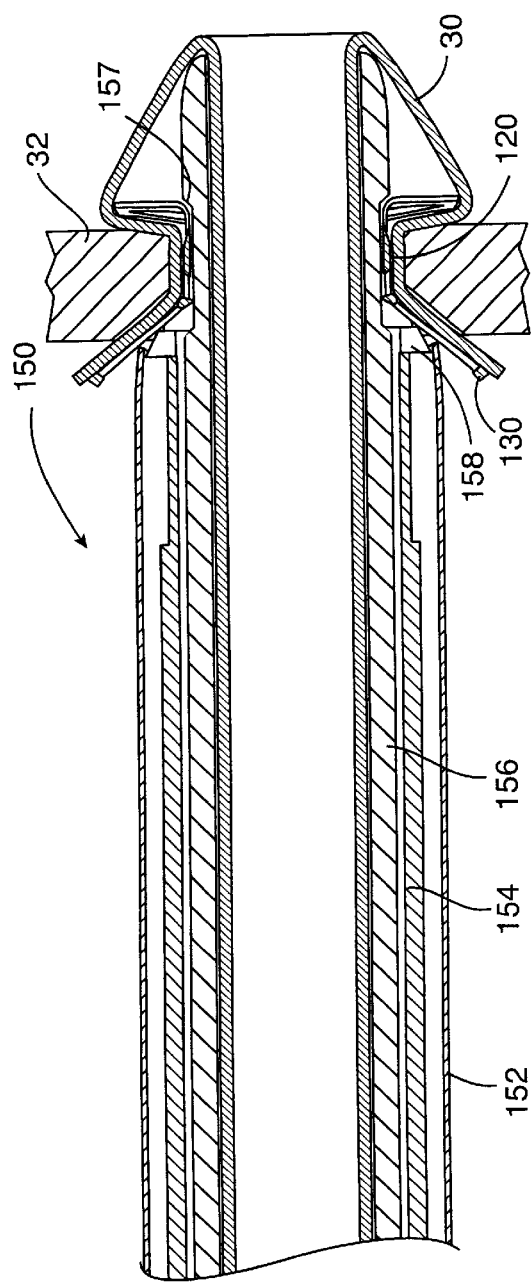

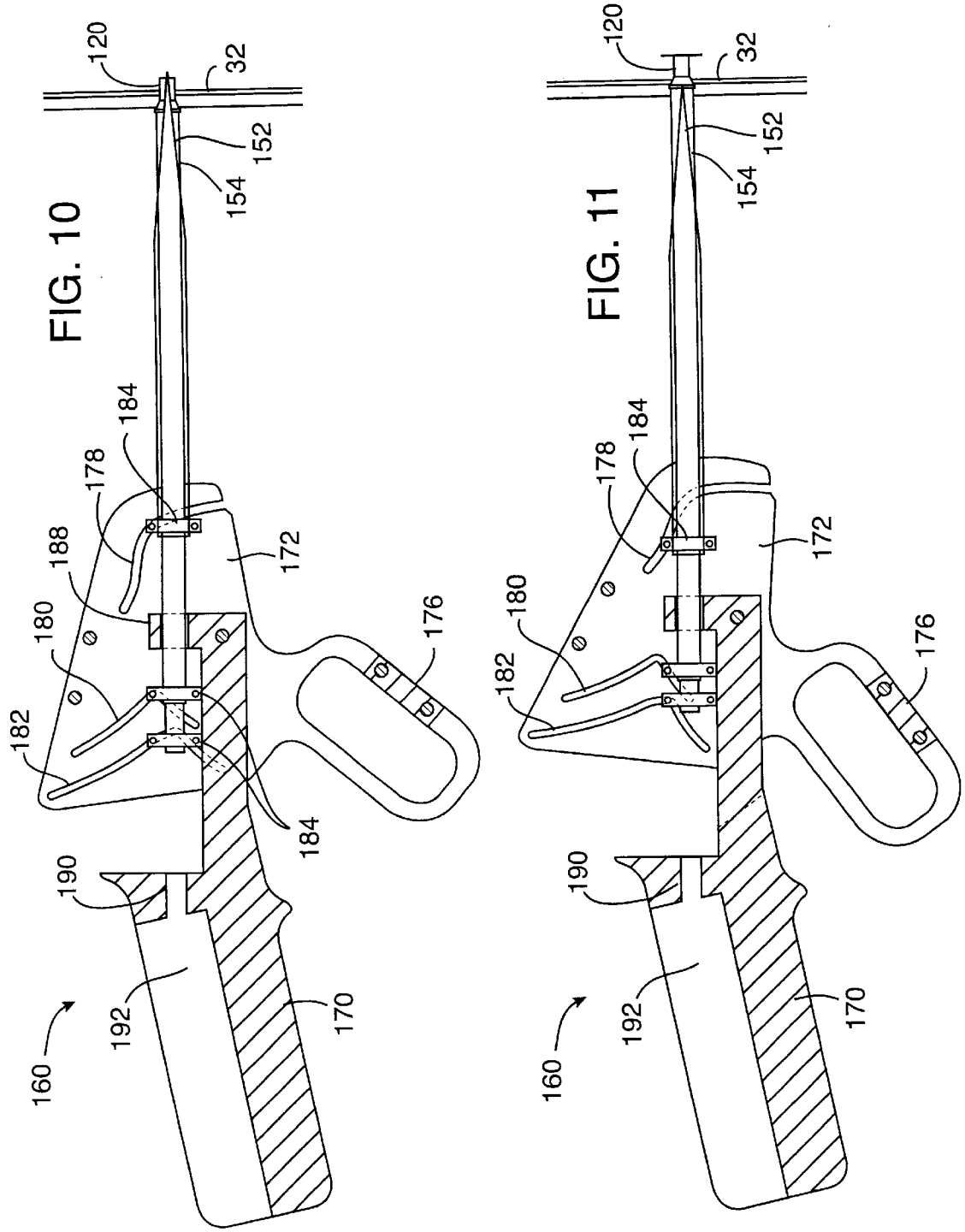

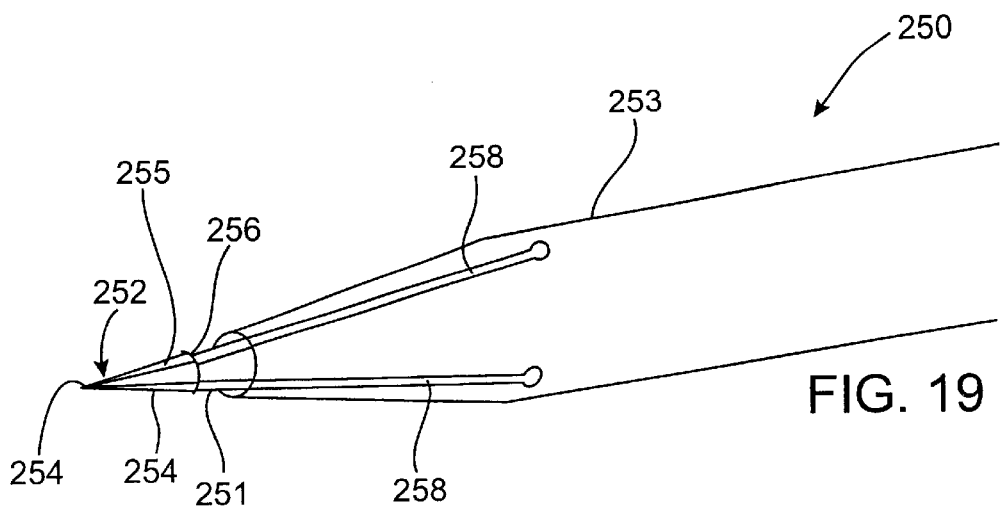
FIG. 19
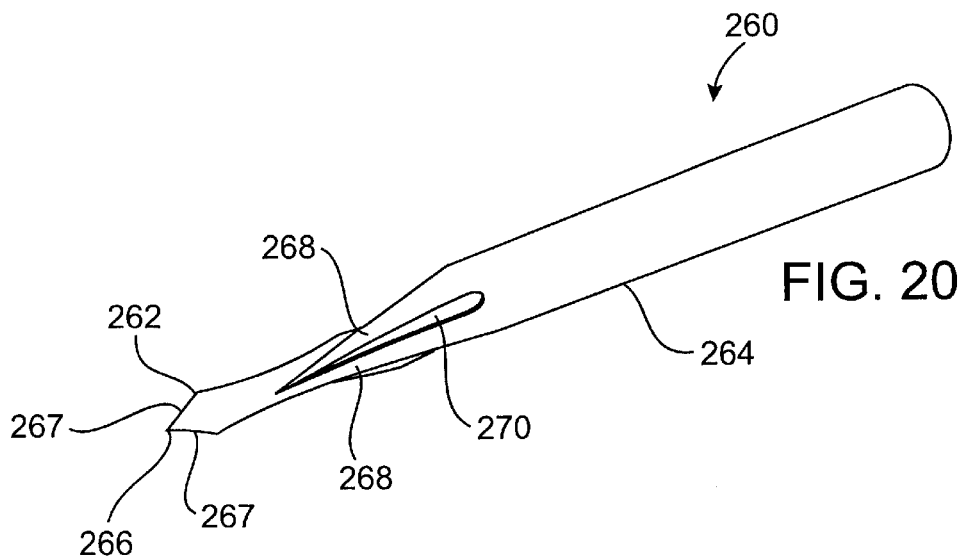
FIG. 20
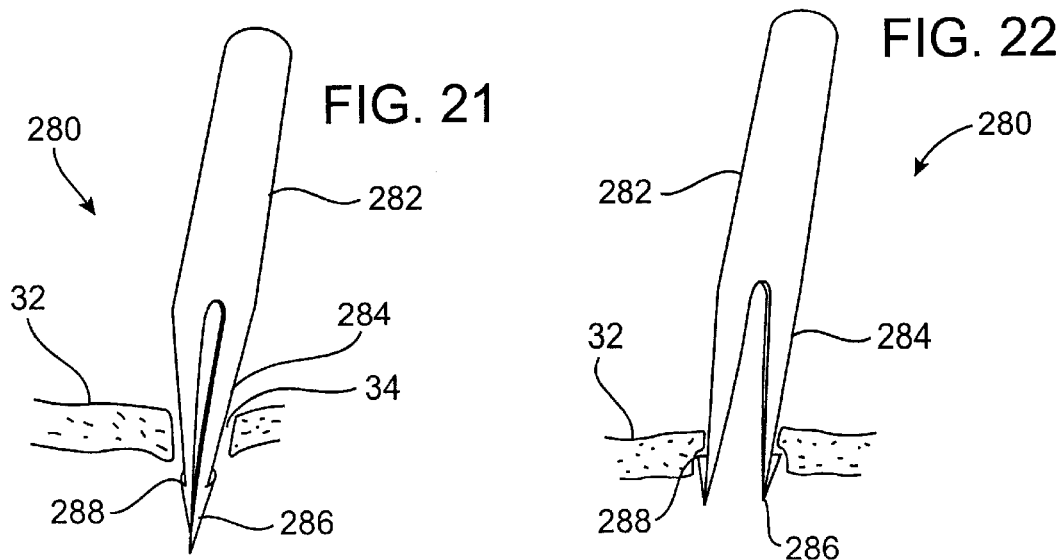
FIG. 21
FIG. 22

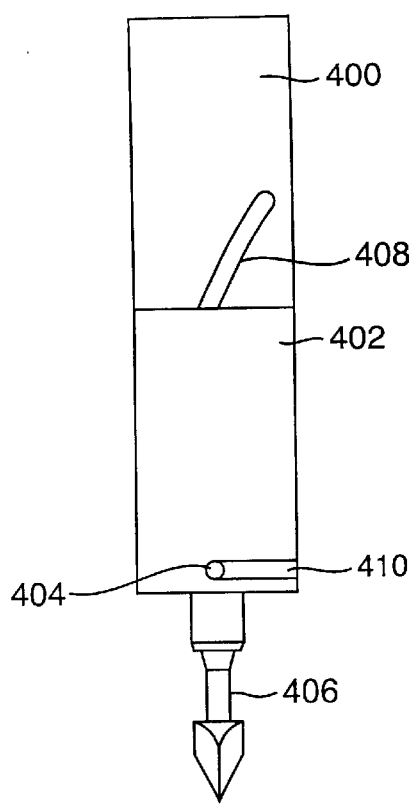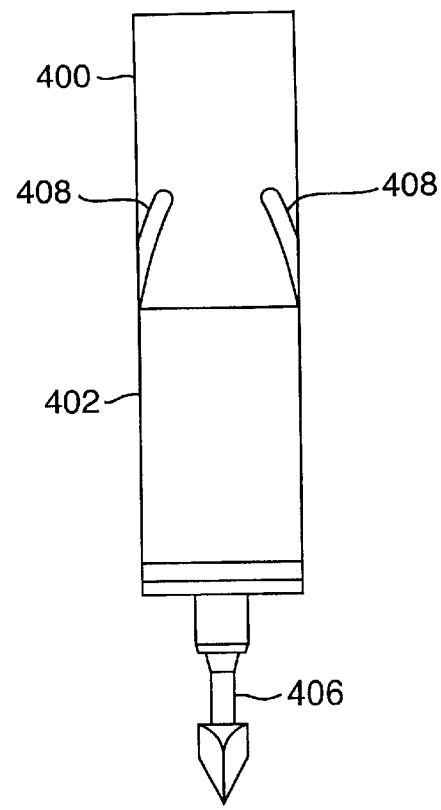
FIG. 40A
FIG. 40B
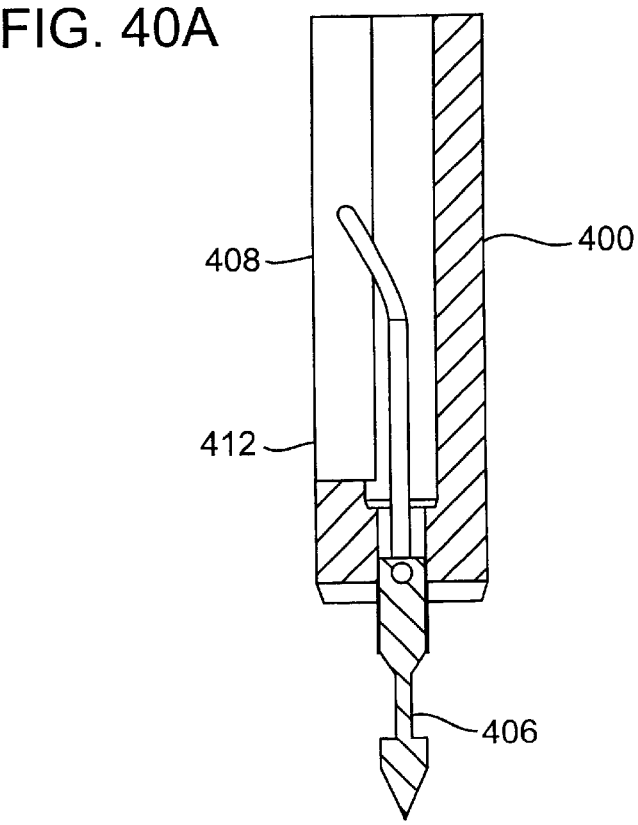
FIG. 40C

TROCAR FOR USE IN DEPLOYING AN ANASTOMOSIS DEVICE AND METHOD OF PERFORMING ANASTOMOSIS

This application is a continuation-in-part of application Ser. No. 09/314,278, filed May, 18, 1999.

BACKGROUND OF THE INVENTION

1. Field of the Invention

The invention relates to a trocar for use during deployment of an anastomosis device and a method of per anastomosis. In a preferred embodiment, the trocar can be used for piercing vessel wall as an initial step in forming a sutureless connection between a bypass graft and a blood vessel.

2. Brief Description of the Related Art

Vascular anastomosis is a procedure by which two blood vessels within a patient are surgically joined together. Vascular anastomosis is performed during treatment of a variety of conditions including coronary artery disease, diseases of the great and peripheral vessels, organ transplantation, and trauma. In coronary artery disease (CAD) an occlusion or stenosis in a coronary artery interferes with blood flow to the heart muscle. Treatment of CAD involves the grafting of a vessel in the form of a prosthesis or harvested artery or vein to reroute blood flow around the occlusion and restore adequate blood flow to the heart muscle. This treatment is known as coronary artery bypass grafting (CABG).

In the conventional CABG, a large incision is made in the chest and the sternum is sawed in half to allow access to the heart. In addition, a heart lung machine is used to circulate the patients blood so that the heart can be stopped and the anastomosis can be performed. During this procedure, the aorta is clamped which can lead to trauma of the aortic tissue and/or dislodge plaque emboli, both of which increase the likelihood of neurological complications. In order to minimize the trauma to the patient induced by conventional CABG, less invasive techniques have been developed in which the surgery is performed through small incisions in the patients chest with the aid of visualizing scopes. Less invasive CABG can be performed on a beating or stopped heart and thus may avoid the need for cardiopulmonary bypass.

In both conventional and less invasive CABG procedures, the surgeon has to suture one end of the graft vessel to the coronary artery and the other end of the graft vessel to a blood supplying vein or artery. The suturing process is a time consuming and difficult procedure requiring a high level of surgical skill. In order to perform the suturing of the graft to the coronary artery and the blood supplying artery the surgeon must have relatively unobstructed access to the anastomosis site within the patient. In the less invasive surgical approaches, some of the major coronary arteries including the ascending aorta cannot be easily reached by the surgeon because of their location. This makes suturing either difficult or impossible for some coronary artery sites. In addition, some target vessels, such as heavily calcified coronary vessels, vessels having very small diameter, and previously bypassed vessels may make the suturing process difficult or impossible.

An additional problem with CABG is the formation of thrombi and atherosclerotic lesions at and around the grafted artery, which can result in the reoccurrence of ischemia. The thrombi and atherosclerotic lesions may be caused by the configuration of the sutured anastomosis site. For example, an abrupt edge at the anastomosis site may cause more stenosis than a more gradual transition.

Accordingly, it would be desirable to provide a sutureless vascular anastomosis device which easily connects a graft to a target vessel. It would also be desirable to provide a sutureless anastomosis device which is formed of one piece and is secured to the target vessel in a single step.

SUMMARY OF THE INVENTION

According to a preferred embodiment, the present invention relates to a trocar for forming an incision in a wall of a target vessel such as an aorta and a deployment tool for delivering an anastomosis device for connecting the end of a graft vessel to a target vessel at the site of the incision. The trocar comprises a member such as a tubular member having a piercing element and the member being adapted to cooperate with a deployment tool such that the anastomosis device can be delivered by the deployment tool and the trocar can be withdrawn from the incision site prior to deployment of the anastomosis device.

The trocar can include various features. For instance, the piercing element can comprise a cutting blade which is movable with respect to the tubular member such that the cutting blade can be moved from a cutting position at which the cutting blade is exposed to a retracted position at which the cutting blade is not exposed. Likewise, the piercing element can comprise a sharpened inclined surface at the distal end of the tubular member. The tubular member can also include distal and proximal portions where the distal portion has a smaller diameter than the proximal portion, and the inclined surface is located on a free end of the distal portion. In addition, the distal portion can include at least one axially extending tear line which allows the distal portion to be split and expanded over the anastomosis device.

According to another embodiment of the invention, the tubular member of the trocar can include a deformable tubular wall. The tubular wall can include openings therein which allow the tubular member to be deformed from a smaller configuration to a larger configuration. The openings can include a plurality of axially extending wall sections and a plurality of circumferentially extending wall sections. The inclined surface can be a continuous surface interrupted by a plurality of slits extending between the inclined surface and the openings closest to the inclined surface. The openings can also include axially extending slots arranged in a staggered pattern such that the circumferentially extending wall sections intersect a pair of slots.

According to another embodiment of the invention, the piercing element can include a vessel wall piercing portion and trimming portion. The piercing portion forms the incision upon insertion of the distal end of the tubular member into the vessel wall and the trimming portion removes tissue around the incision upon retraction of the tubular member. The piercing element can also include a plurality of axially extending tines at the distal end of the tubular member. In this manner, the trimming portion is formed as the cutting edges on outer surfaces of the tines, which remove the tissue upon retraction from the tubular member.

According to another embodiment of the invention, the piercing element can include a cutting blade which forms an elongated slit upon insertion of the piercing element into the vessel wall. The tubular member can include tines at the distal end thereof, the tines being separated from each other and from the cutting blade by axially extending slits. The distal ends of the tines can be biased in close proximity to each other at a location spaced from the distal end of the cutting blade. The cutting blade can include two cutting edges which meet at a point and form an angle therebetween. The piercing element can also comprise a flat pointed blade sized to provide the incision with a size smaller than the anastomosis device in an expanded condition.

In accordance with an additional aspect of the present invention, a method of performing anastomosis includes the step of using a trocar to form an incision in a wall of a target vessel such as an aorta. The anastomosis device is then inserted into the incision through the trocar. The first portion is manipulated with respect to a second portion of the anastomosis device to capture edges of the incision in the target vessel with the anastomosis device such that a fluid passage is established between the graft vessel and the target vessel.

Preferably, the target vessel is an aorta and the method is performed without occlusion (i.e., clamping) of the aorta. The end of the graft vessel and the edges of the incision in the target vessel can be captured between the first portion and the second portion so that the end of the graft vessel abuts an outside wall of the target vessel. The anastomosis device can be expandable from a first configuration to a larger second configuration where the anastomosis device is expanded with an expander to cause a portion of the anastomosis device to fold outward forming the first flange. In this regard, the first flange holds a portion of the graft vessel in contact with an inner surface of the target vessel.

The method can also include the step of retracting the trocar over the anastomosis device and along the expander prior to expanding the anastomosis device with the expander where the trocar is deformed during the retracting step. Preferably, the second flange can be formed by axially compressing the anastomosis device with a deployment tool. The deployment tool can comprise a tube which engages a proximal end of the anastomosis device where the compression step is carried out by withdrawing the expander through the tube. A groove on the expander can engage tabs on the anastomosis device during formation of the second flange.

According to another aspect of the invention, the anastomosis device can be severed into a deployed portion and a discard portion during the step of forming the second flange. The anastomosis device can comprise an expandable linkage which is delivered through the trocar to the site of the incision, the linkage being deformed to an expanded size during formation of the first and second flanges, the incision formed by the trocar being smaller than the expanded size. Finally, the first and second flanges can form an angle between 40 and 140 degrees with an axis of the anastomosis device.

BRIEF DESCRIPTION OF THE DRAWINGS

The invention will now be described in greater detail with reference to the preferred embodiments illustrated in the accompanying drawings, in which like elements bear like reference numerals, and wherein:

FIG. 7 is a side cross sectional view of the anastomosis device deployment system with an expanded first annular flange;

FIG. 8 is a side cross sectional view of the anastomosis device deployment system expanding a second annular flange;

FIG. 10 is a schematic side cross-sectional view of the deployment tool of FIG. 9 shown during an anastomosis device insertion step;

FIG. 11 is a schematic side cross-sectional view of the deployment tool of FIG. 9 shown during an anastomosis device expansion step;

FIG. 19 is a perspective view of a trocar according to a fourth alternative embodiment of the invention;

FIG. 20 is a perspective view of a trocar according to a fifth alternative embodiment of the invention;

FIG. 21 is a perspective view of a trocar according to a sixth alternative embodiment of the invention showing the trocar in a cutting position.

FIG. 22 is a perspective view of the trocar according to FIG. 22 showing the trocar in a retracted position;

FIGS. 40A–C and 41A–C are perspective views of a trocar according to a fourteenth alternative embodiment of the invention wherein a one-piece piercing element can be retracted by a pin and slot arrangement to a storage position within an introducer sheath.

DETAILED DESCRIPTION OF THE PREFERRED EMBODIMENTS

Figure 1:
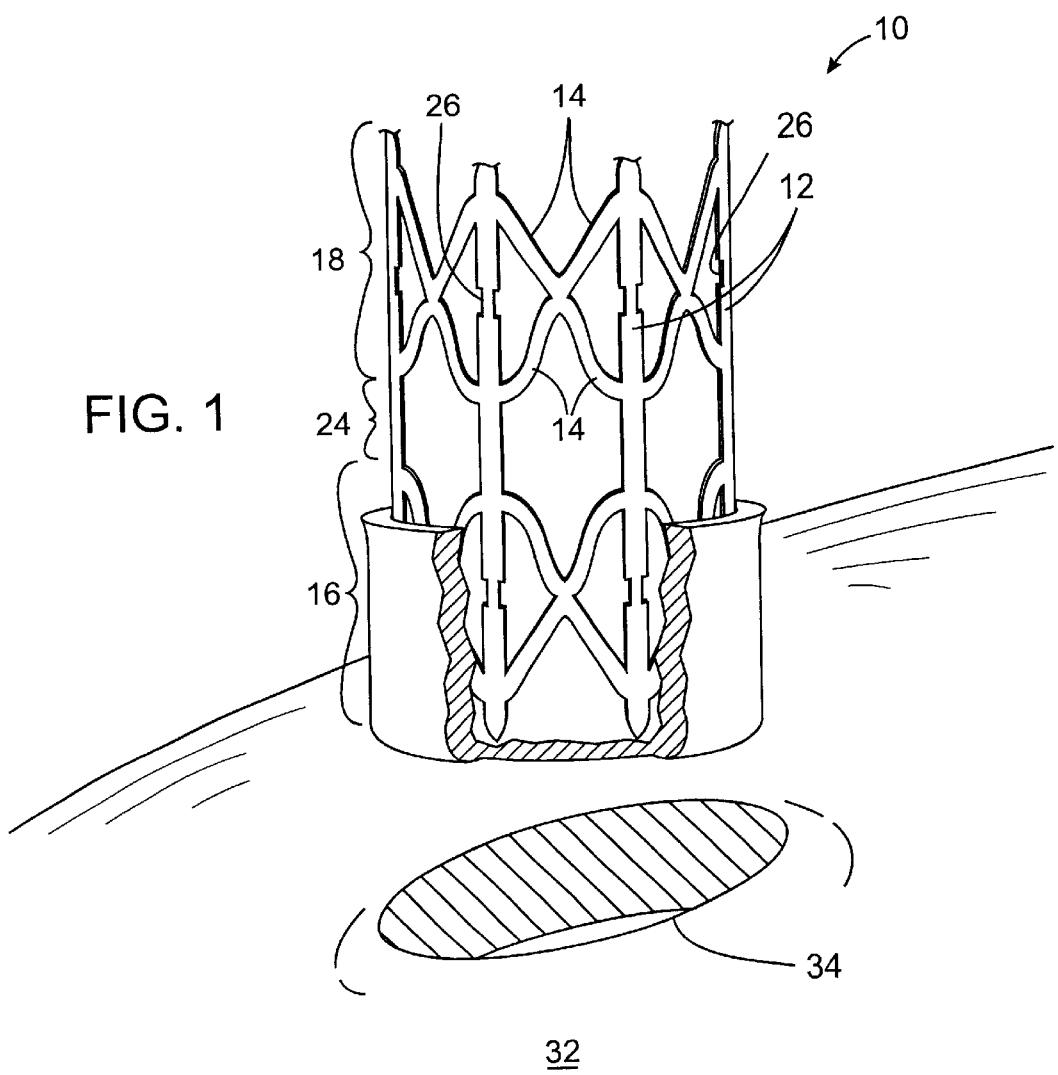
FIG. 1 is a perspective view of a first embodiment of an anastomosis device in a configuration prior to use with a graft vessel everted over the device.

According to the invention it is possible to perform a variety of anastomosis procedures, including coronary artery bypass grafting. The term "target vessel" is thus used to refer to vessels within the patient which are connected to either or both of the upstream and downstream end of the graft vessel. In such procedures, a large vessel anastomotic device is used with large diameter target vessels such as the aorta or its major side branches.

In deploying a large vessel anastomotic device, the device (with one end of a graft vessel attached thereto) is inserted into an incision in a wall of the target vessel with a deformable section in a first configuration, and the deformable section is radially expanded to a second configuration to deploy a flange. The flange applies an axial force against the wall of the target vessel. Additionally, the flange can be configured to apply a radial force, substantially transverse to the device longitudinal axis, against the wall of the target vessel, to secure the device to the target vessel. For example, the device can have a plurality of deformable sections forming distal and proximal flanges. With the proximal and distal end flanges deployed, the device can be prevented from shifting proximally out of the target vessel or distally farther into the interior of the target vessel.

The large vessel devices can be configured to connect to target vessels of various sizes having a wall thickness of at least about 0.5 mm, and typically about 0.5 mm to about 5 mm. In a preferred embodiment of the invention, the large vessel anastomotic device is configured to longitudinally collapse as the deformable section is radially expanded. The surgeon can control the longitudinal collapse to thereby position the distal end flange at a desired location at least partially within the incision in the target vessel wall. The surgeon can also control the position of the proximal end flange by longitudinally collapsing the device to a greater or lesser degree, to thereby position the proximal end flange at a desired location in contact with the target vessel. Thus, regardless of the thickness of the target vessel wall, the device can be longitudinally collapsed to position the flanges against the target vessel wall and effectively connect the device thereto. This feature is significant because the device must be connected to target vessels which have a wide range of wall thickness. For example, the aortic wall thickness is typically about 1.4 mm to about 4.0 mm and the aorta diameter can range from about 25 to about 65 mm in diameter. Therefore, regardless of the thickness of the target vessel wall, the degree of deployment of the proximal end flange, and thus the longitudinal collapse of the device, can be controlled by the physician to thereby effectively connect the device to the target vessel. For example, the surgeon may choose between partially deploying the proximal end flange so that it is positioned against an outer surface of the target vessel wall, or fully deploying the flange to position it in contact with the media of the target vessel wall within the incision in the target vessel wall.

In a coronary bypass operation in accordance with the invention, a large vessel device can be used to connect the proximal end of the graft vessel to the aorta. However, in patients with an extreme arteriosclerotic lesion in the aorta, which may result in serious complications during surgical procedures on the aorta, the surgeon may wish to avoid this region and connect the proximal end of the graft vessel to any other adjacent less diseased vessel, such as the arteries leading to the arms or head. Further, the devices can be used with venous grafts, such as a harvested saphenous vein graft, arterial grafts, such as a dissected mammary artery, or a synthetic prosthesis, as required.

Connection of the large vessel device does not require the stoppage of blood flow in the target vessel. Moreover, the anastomotic devices can be connected to the target vessel without the use of cardiopulmonary bypass. In contrast, anastomosis techniques wherein the aorta is clamped to interrupt blood flow to the area of the aortic wall to which a vein is to be anastomosed may result in liberation of plaques and tissue fragments which can lead to organ dysfunction, such as strokes, renal failure, or intestinal ischemia. However, severely diseased aortas may not provide an area suitable for clamping due to significant calcification of the aortic wall. In the anastomosis technique according to the invention, the surgeon does not need significant room inside the patient to connect the anastomotic devices to the target vessel. For example, unlike sutured anastomoses which require significant access to the aorta for the surgeon to suture the graft vessel thereto, the anastomotic devices allow the proximal end of the graft vessel to be connected to any part of the aorta. All parts of the aorta are accessible to the large vessel anastomosis devices, even when minimally invasive procedures are used. Consequently, the graft vessel may be connected to the descending aorta, so that the graft vessel would not be threatened by damage during a conventional sternotomy if a second operation is required at a later time.

According to the invention, a sutureless connection can be provided between a graft and a target vessel, while minimizing thrombosis or restenosis associated with the anastomosis. The anastomotic devices can be attached to the target vessel inside a patient remotely from outside the patient using specially designed applicators, so that the devices are particularly suitable for use in minimally invasive surgical procedures where access to the anastomosis site is limited. The devices allow the anastomosis to be performed very rapidly, with high reproducibility and reliability, without clamping, and with or without the use of cardiopulmonary bypass.

According to one preferred method of deploying the anastomosis device, the surgeon operates a deployment tool using both hands. One hand supports the tool via a handle while the other twists an actuation knob to deploy the anastomotic device. Locating the actuation knob on the tool's main axis minimizes the tendency of reaction forces to wobble the tool keeping it stable and in proper position during deployment. The twisting motion is converted to linear displacements by a set of rotating cams that engage a trocar, holder, and expander. The cams control the sequence of relative motions between the instrument's trocar and device deployment mechanisms.

During the foregoing procedure, a surgeon will place the tip of the instrument (the mechanical stop) in light contact with the site on the aorta to be anastomosed. Having located a suitable site, the surgeon then twists the actuation knob to fire the spring-loaded trocar and continues twisting to deploy the anastomotic device. The trocar penetrates the aortic wall at a high rate of speed to minimize any unintended deformation of the aorta and maintains a substantially fluid-tight seal at the puncture site. Having entered the aortic lumen, the trocar dilates as the anastomotic device and its holder tube (crown) are advanced through it, thus retracting the aortic tissue and serving as an introducer for the device. Once the device has fully entered the aortic lumen the trocar is withdrawn. The anastomotic device is then expanded to its fall diameter and an inner flange is deployed. The device is then drawn outwards towards the instrument (mechanical stop) to seat the inner flange firmly against the intimal wall of the aorta. An outer flange is then deployed from the external side, compressing the aortic wall between the inner and outer flanges and the device is disengaged from the instrument completing the anastomosis.

Figure 2:
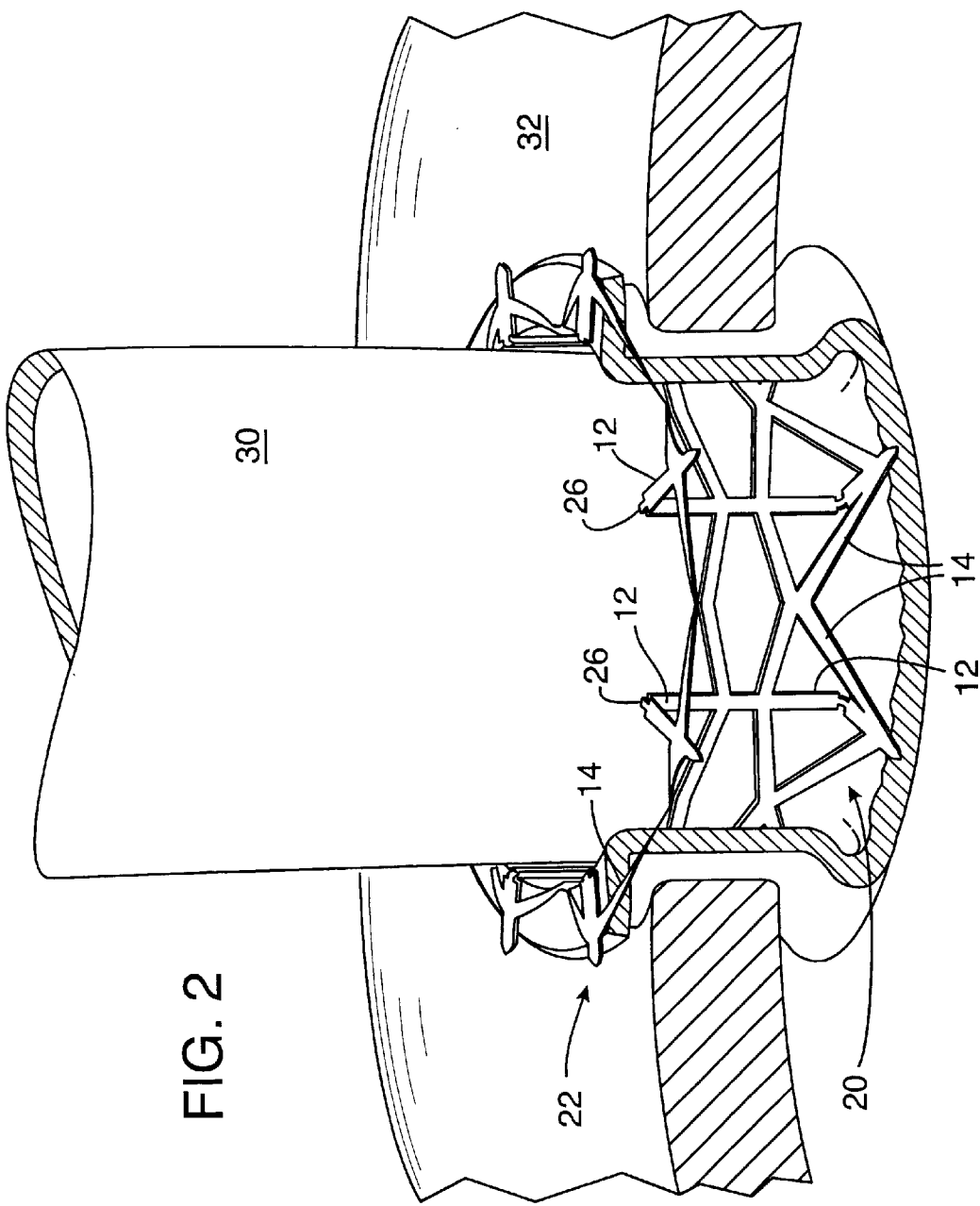
FIG. 2 is a perspective view of the anastomosis device of FIG. 1 in a deployed configuration.

FIG. 1 illustrates the distal portion of an anastomosis device 10 according to a first embodiment of the present invention, the proximal portion (not shown) being adapted to be deployed by a deployment tool which will be explained later. The anastomosis device 10 includes a plurality of axial members 12 and a plurality of struts 14 interconnecting the axial members. The axial members 12 and struts 14 form a first linkage 16 at a first end of the device and a second linkage 18 at a second end of the device. The first and second linkages 16, 18 form inner and outer flanges 20, 22 when the anastomosis device 10 is deployed as illustrated in FIG. 2. The deployed flanges 20, 22 may be annular ring shaped or conical in shape. The first and second linkages 16, 18 are connected by a central connecting portion 24.

In use, a graft vessel 30 is inserted through a center of the tubular anastomosis device 10 and is everted over the first linkage 16 at the first end of the device. The first end of the device may puncture part way or all the way through the graft vessel wall to hold the graft vessel 30 on the device. An opening 34 is formed in the target vessel 32 to receive the graft vessel 30 and anastomosis device 10. Once the anastomosis device 10 with everted graft vessel 30 are inserted through the opening 34 in the target vessel 32, the inner and outer flanges 20, 22 are formed as shown in FIG. 2 to secure the graft vessel to the target vessel by trapping the wall of the target vessel between the two flanges. The anastomosis device 10 forms a smooth transition between the target vessel 32 and the graft vessel 30 which helps to prevent thrombi formation.

The inner and outer flanges 20, 22 are formed by radial expansion of the anastomosis device 10 as follows. The first and second linkages 16, 18 are each made up of a plurality of axial members 12 and struts 14. The struts 14 are arranged in a plurality of diamond shapes with adjacent diamond shapes connected to each other to form a continuous ring of diamond shapes around the device. One axial member 12 extends through a center of each of the diamond shapes formed by the struts 14. A reduced thickness section 26 or hinge in each of the axial members 12 provides a location for concentration of bending of the axial members. When an expansion member of a deployment tool such as a rod or balloon is inserted into the tubular anastomosis device 10 and used to radially expand the device, each of the diamond shaped linkages of struts 14 are elongated in a circumferential direction causing a top and bottom of each of the diamond shapes to move closer together. As the top and bottom of the diamond shapes move closer together, the axial members 12 bend along the reduced thickness sections 26 folding the ends of the device outward to form the inner and outer flanges 20, 22 with the result that the wall of the target vessel 32 is trapped between the flanges and the everted graft vessel 30 is secured to the target vessel.

In the anastomosis device 10 shown in FIGS. 1 and 2, the struts 14 may be straight or curved members having constant or varying thicknesses. In addition, the axial members 12 may have the reduced thickness sections 26 positioned at a center of each of the diamond shapes or off center inside the diamond shapes. The positioning and size of the reduced thickness sections 26 will determine the location of the flanges 20, 22 and an angle the flanges make with an axis of the device when fully deployed. A final angle between the flanges 20, 22 and longitudinal axis of the device 10 is about 40 to 140 degrees, preferably about 50–90 degrees.

Figure 3:
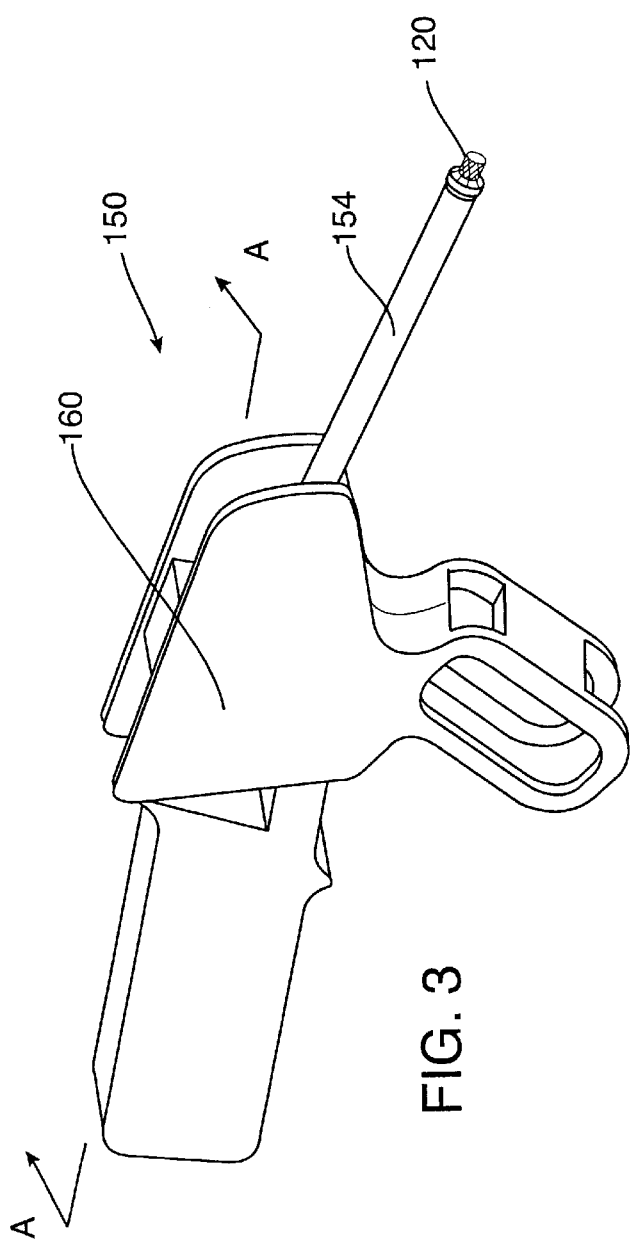
FIG. 3 is a perspective view of an anastomosis device deployment system.
Figure 4:
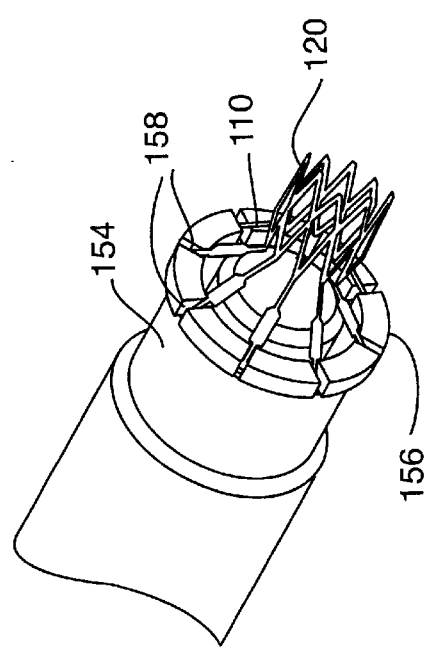
FIG. 4 is an enlarged perspective view of the distal end of the anastomosis device deployment system of FIG. 3 with an anastomosis device prior to deployment.
Figure 5:
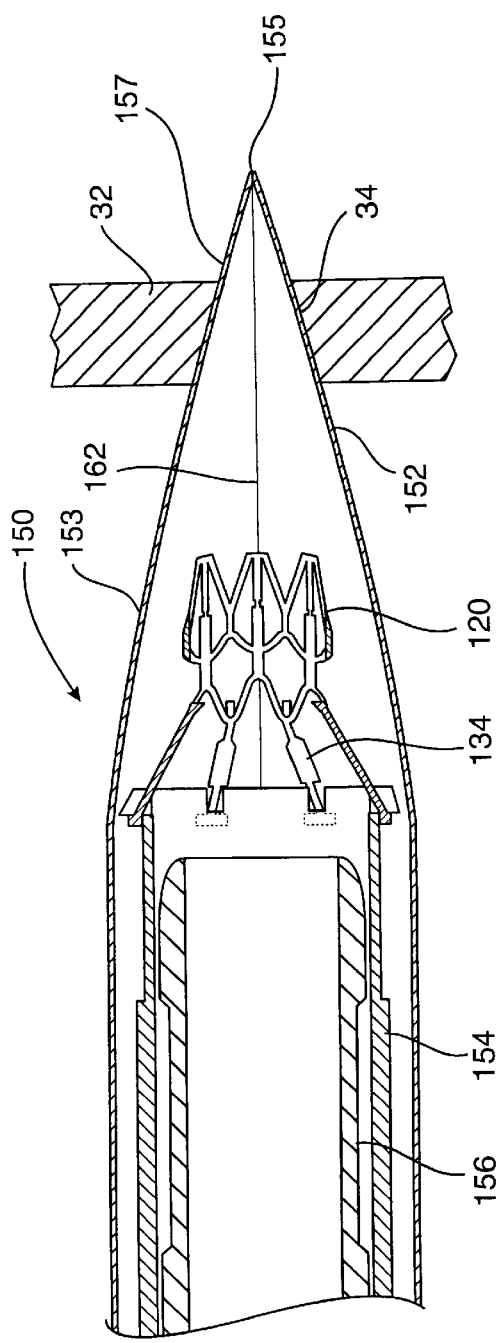
FIG. 5 is a side cross sectional view of the anastomosis device deployment system puncturing the target vessel to advance the anastomosis device into the target vessel wall.

FIGS. 3–7 illustrate a deployment system 150 and sequence of deploying an anastomosis device 120 such as the device shown in FIGS. 1–2 with the deployment system. In FIGS. 3–5 the graft vessel 30 has been eliminated for purposes of clarity. As shown in FIGS. 3–7, the deployment system 150 includes a hollow outer trocar 152 (not shown in FIG. 3), a holder tube 154 positioned inside the trocar, and an expander tube 156 slidable inside the holder tube. As can be seen in the detail of FIG. 4, the anastomosis device 120 is attached to a distal end of the holder tube 154 by inserting T-shaped ends 112 of pull tabs 110 in slots 158 around the circumference of the holder tube. The trocar 152, holder tube 154, and expander tube 156 are all slidable with respect to one another during operation of the device. A device handle 160 is provided for moving the tubes with respect to one another will be described in further detail below with respect to FIGS. 8–11.

Figure 6:
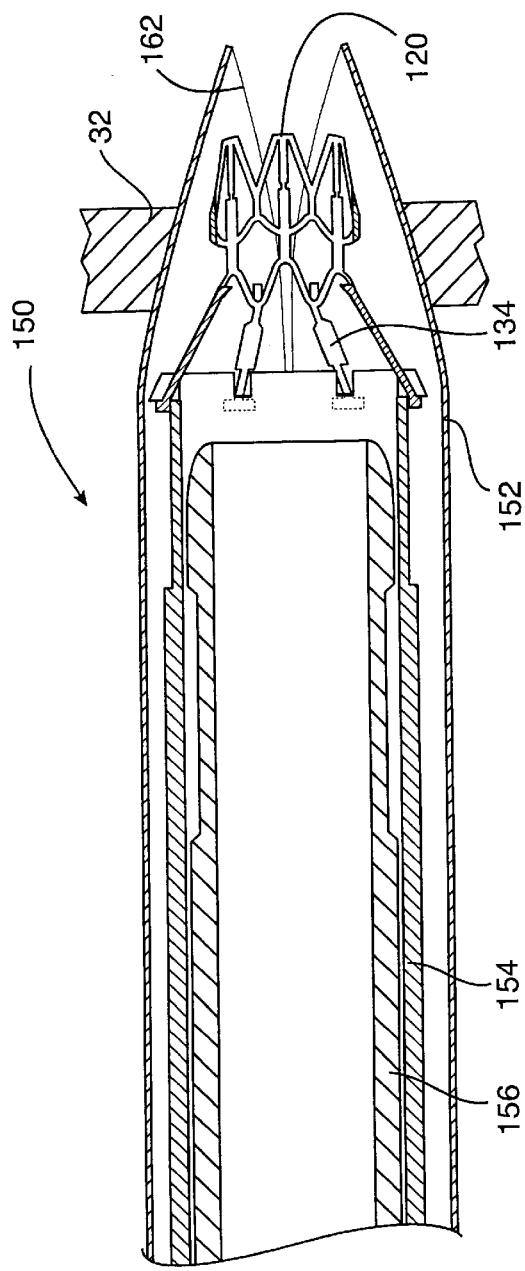
FIG. 6 is a side cross sectional view of the anastomosis device deployment system advancing the anastomosis device into the target vessel wall.

As shown in FIG. 5, initially, the holder tube 154, expander tube 156, and the anastomosis device 120 are positioned within the trocar 152 for insertion. The trocar 152 has a hollow generally conical tip 153 with a plurality of axial slots 162 which allow the conical tip 153 to be spread apart so that the anastomosis device 120 can slide through the opened trocar. The conical tip 153 of the trocar 152 includes a piercing element 155 at its distal end 157. The trocar 152, acting as a tissue retractor and guide, is inserted through the wall of the target vessel 32 by way of piercing element 155 to form an opening 34. As shown in FIG. 6, the anastomosis device 120 is then advanced into or through the target vessel wall 32 with the holder tube 154. The advancing of the holder tube 154 causes the distal end of the trocar 152 to be forced to spread apart. Once the anastomosis device 120 is in position and the trocar 152 has been withdrawn, the inner annular flange 20 is deployed by advancing the expander tube 156 into the anastomosis device. The advancing of the expander tube 156 increases the diameter of the anastomosis device 120 causing the inner flange to fold outward from the device. This expanding of the inner flange may be performed inside the vessel and then the device 120 may be drawn back until the inner flange abuts an interior of the target vessel wall 32.

As shown in FIG. 8, after the inner flange has been deployed, the holder tube 154 is advanced forming the outer flange. As the holder tube 154 is advanced, the anastomosis device 120 drops into a radial groove 157 on an exterior of the expander tube 156 which holds the anastomosis device stationary on the expander tube 156. The holder tube 154 is then moved forward to detach the entire anastomosis device by disengaging the pull tabs 130 from the slots 158 in the holder tube and causing the outer flange to be deployed.

During deployment of the outer flange, shoulders 134 on the device, shown most clearly in FIGS. 5 and 6, engage a tapered distal end of the holder tube 154 causing the pull tabs 130 to be released from the slots 158. Alternatively, and as will be explained in connection with a frangible anastomosis device according to the invention, movement of the holder tube 154 can detach a deployed portion of the device from a throw away portion of the device which remains attached to the holder tube.

One alternative embodiment of the holder tube 154 employs a plurality of flexible fingers which receive the pull tabs 130 of the anastomosis device 120. According to this embodiment each pull tab 130 is received by an independent finger of the holder tube 154. To deploy the second or outer flange of the anastomosis device 120, the flexible fingers flex outward bending the pull tabs 130 outward.

FIGS. 9–12 illustrate the operation of the handle 160 to move the trocar 152, the holder tube 154, and the expander tube 156 with respect to one another to deploy the anastomosis device 120 according to the present invention. The handle 160 includes a grip 170 and a trigger 172 pivotally mounted to the grip at a pivot 174. The trigger 172 includes a finger loop 176 and three contoured cam slots 178, 180, 182 corresponding to the trocar 152, holder tube 154, and expander tube 156, respectively. Each of these tubes has a fitting 184 at a distal end thereof. A pin 186 connected to each of the fittings 184 slides in a corresponding one of the cam slots 178, 180, 182. A fourth cam slot and tube may be added to control deployment of the outer flange. Alternatively, the handle can be modified to include fewer cam slots for deployment of the inner and outer flanges.

The handle 160 is shown in FIG. 8 in an insertion position in which the trocar 152 extends beyond the holder tube 154 and the expander tube 156 for puncturing of the target vessel wall 32. Optionally, a flexible seal (not shown) such as heat shrinkable plastic tubing or a molded elastomer can be provided on the outer surface of the trocar 152 such that the seal covers the axial slots 162 at a location spaced from the tip of the trocar to minimize leaking of blood from the target vessel after the incision is formed. As the trigger 172 is rotated from the position illustrated in FIG. 9 to the successive positions illustrated in FIGS. 10–12, the pins 186 slide in the cam slots 178, 180, 182 to move the trocar 152, holder tube 154 and expander tube 156.

Figure 9:
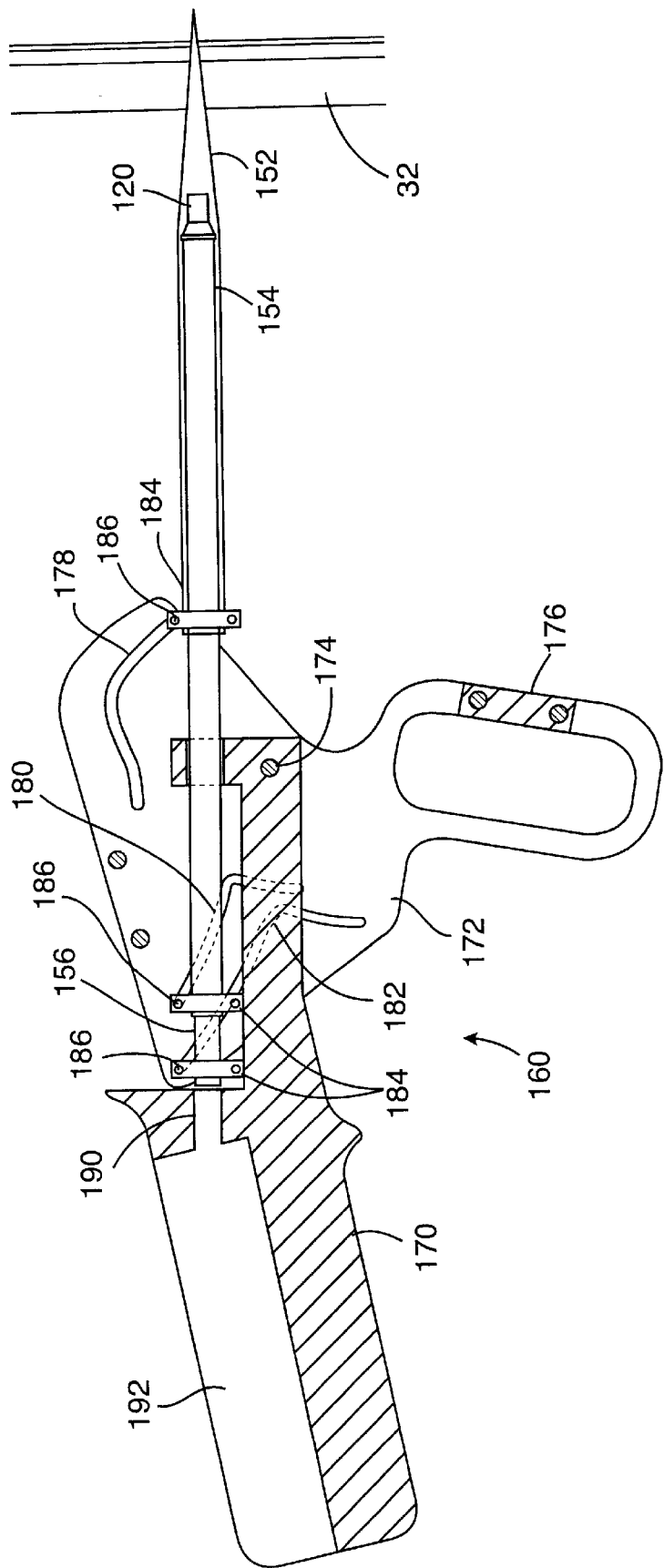
FIG. 9 is a schematic side cross-sectional view of a deployment tool taken along line A—A of FIG. 3, the deployment tool is shown during a vessel puncturing step.

FIG. 10 shows the handle 160 with the trigger 172 rotated approximately 30 degrees from the position of FIG. 9. This rotation moves the holder tube 154 and expander tube 156 forward into the wall of the target vessel 32 spreading the trocar 152. The anastomosis device 120 is now in position for deployment. FIG. 11 shows the trigger 172 rotated approximately 45 degrees with respect to the position of FIG. 9 and the cam slot 182 has caused the expander tube 156 to be advanced within the holder tube 154 to deploy the inner flange. The trocar 152 has also been withdrawn.

Figure 12:
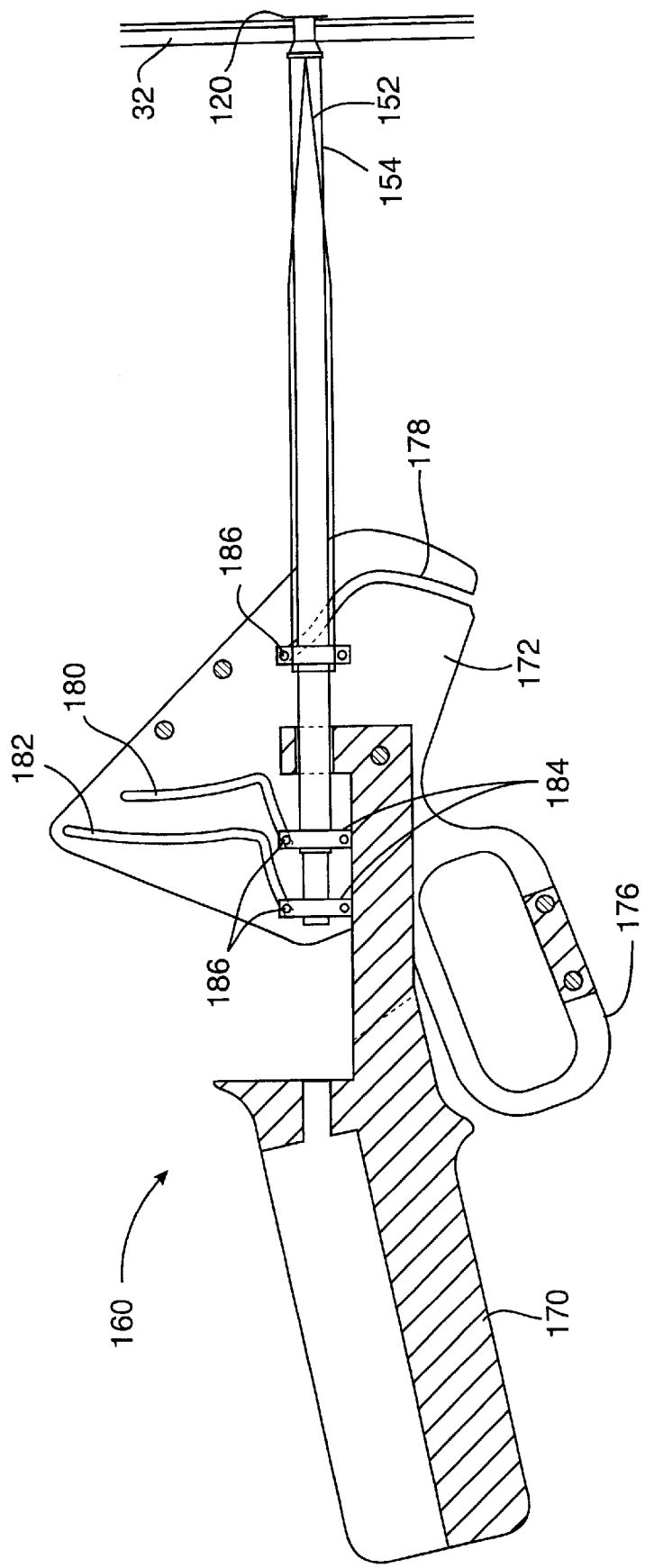
FIG. 12 is a schematic side cross-sectional view of the deployment tool of FIG. 9 shown after the anastomosis device has been fully deployed.

FIG. 12 shows the handle 160 with the trigger 172 pivoted approximately 60 degrees with respect to the position shown in FIG. 9. As shown in FIG. 12, the expander tube 156 has been withdrawn to pull the inner flange against the vessel wall 32 and the holder tube 154 is moved forward to deploy the outer flange and disengage the holder tube 154 from the anastomosis device 120.

The handle 160 also includes a first channel 188 and a second channel 190 in the grip 170 through which the graft vessel (not shown) may be guided. The grip 170 also includes a cavity 192 for protecting an end of the graft vessel opposite from the attachment end.

FIGS. 13–23 show alternative embodiments of the trocar 152 of FIGS. 3–7. The trocar is preferably designed so that it can punch through the tissue of the target vessel wall 32 with minimal tearing but permit spreading of the tissue to allow insertion of the anastomosis device through the tubular or hollow tip 153 of the trocar 152. In several of the following embodiments the trocar includes a tubular member through which the anastomosis device is delivered to the interior of the target vessel. However, arrangements other than the tubular member could be used. In a preferred embodiment, the trocar is actuated by a mechanism which causes the trocar to penetrate the aorta wall at a high rate of speed to minimize deformation of the aorta and maintain a substantially fluid tight seal at the puncture site in a manner similar to a biopsy gun. For instance, a spring mechanism attached to the trocar and/or the handle can be used to fire the trocar at the incision site a preset distance such as around 13 mm. Any suitable actuating mechanism can be used to fire the trocar in accordance with the invention.

Figure 13:
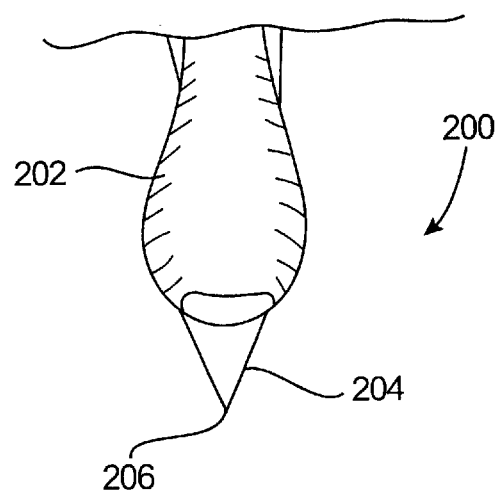
FIG. 13 is a front elevational view of a trocar according to a first alternative embodiment of the invention.
Figure 14:
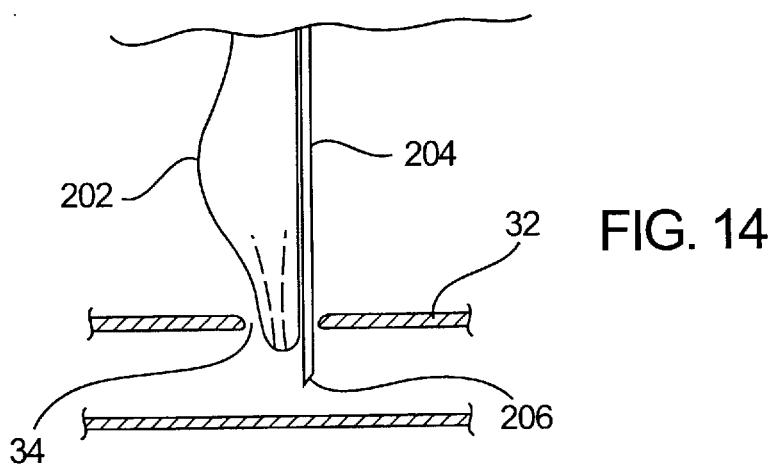
FIG. 14 is a side cross sectional view of the trocar of FIG. 13 with the blade in the cutting position.
Figure 15:
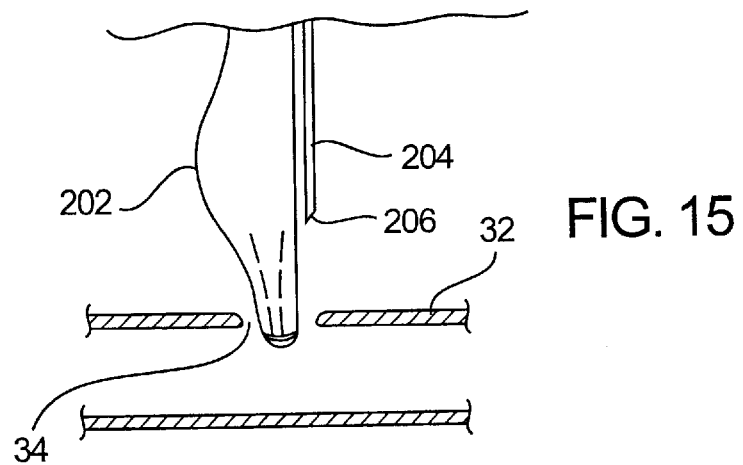
FIG. 15 is a side cross sectional view of the trocar of FIG. 13 with the blade in the retracted position.

FIG. 13 shows a trocar 200 according to a first alternative embodiment. The trocar 200 includes a tubular member 202 having a piercing element 204 at its distal end. The interior of the tubular member 202 forms a passage for delivery of the anastomosis device 120. The piercing element 204 includes a cutting blade 206 and is movable with respect to the tubular member 202. This allows the cutting blade 206 to be moved between a cutting position where the cutting blade 206 is exposed, as shown in FIG. 14, to a retracted position where the cutting blade 206 is not exposed, as shown in FIG. 15.

The tubular member 202 is preferably deformable, and can be made from materials such as plastic and/or metal. If made from a rigid material, the tubular member 202 may include one or more weakened areas such as tear lines which allow the tubular member 202 to be split and stripped over the holder tube 154 (FIGS. 3–7).

In operation, the cutting blade 206 is inserted into and punctures the target vessel wall 32 to form an opening 34. The size of the incision formed by the flat blade 206 is preferably no greater than the size of the unexpanded anastomosis device to be inserted in the incision. Once the opening 34 is formed, a portion of the tubular member 202 moves into the opening 34, as shown in FIG. 14. Preferably, the trocar 200 has a flattened tapering shape to stretch or expand the opening 34 formed by the cutting blade 206. After a portion of the tubular member 202 becomes positioned within the opening 34, the blade 206 is retracted. The anastomosis device 120 is then deployed into or through the target vessel wall 32 as shown in FIG. 6 and as described above. During such delivery, since the blade 206 is retracted, the flattened shape of the tubular member can be deformed into a cylindrical shape.

Figure 16:
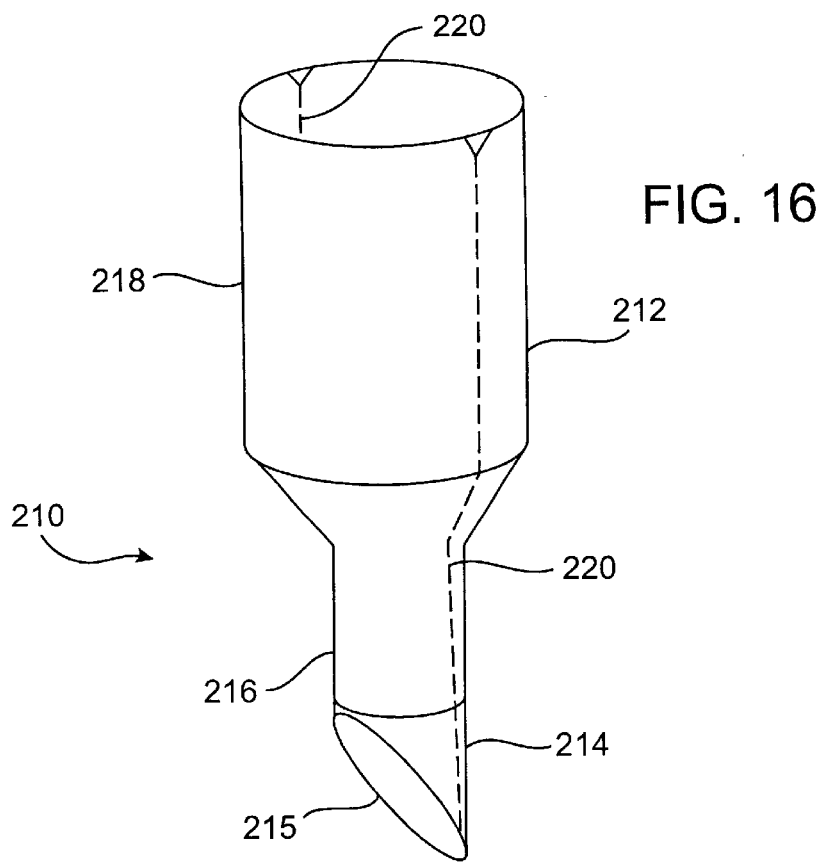
FIG. 16 is a perspective view of a trocar according to a second alternative embodiment of the invention.
Figure 17:
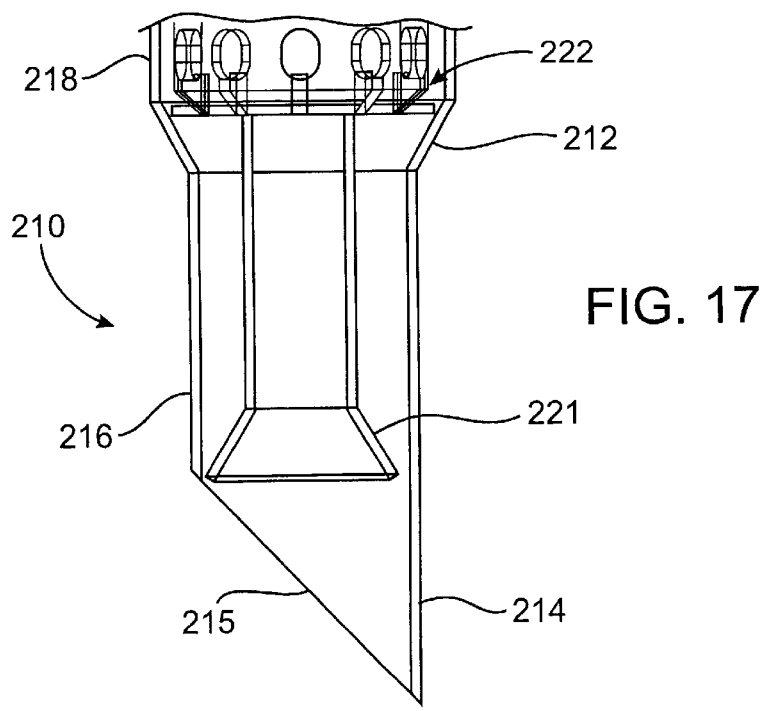
FIG. 17 is a cross sectional view of the trocar according to FIG. 16.

FIGS. 16–17 show a trocar 210 according to a second alternative embodiment. The trocar 210 includes a tubular member 212 having a piercing element 214 at its distal end. The piercing element 214 is shaped as an inclined surface 215 at the distal end of the tubular member 212. The tubular member 212 includes distal and proximal portions 216 and 218, respectively. The distal portion 216 has a smaller diameter then the proximal portion 218, and the inclined surface 215 is disposed on a free end of the distal portion 216. Preferably, the tubular member 212 includes axial extending tear lines 220 which allow the distal portion 216 to be split and retracted over the holder tube.

To deploy the anastomosis device according to this embodiment, the distal portion 216 is inserted into the target vessel wall, as described above. In the process of piercing the target vessel wall, the beveled tip of the trocar expands the incision opening to a diameter larger than the unexpanded anastomosis device. The anastomosis device having a graft vessel everted thereover (shown generally at 221) is supported on a distal end of the holder tube 222 within the distal portion 216, as shown in FIG. 17. The piercing element 215 punctures the target vessel wall, and carries the anastomosis device within the target vessel wall. The tubular piercing element 215 and tubular member 212 are then retracted from the target vessel wall over the holder tube 222 with the result that the distal portion 216 splits along tear lines 220 as it stretches over the bevel on the end of the holder tube.

Figure 18:
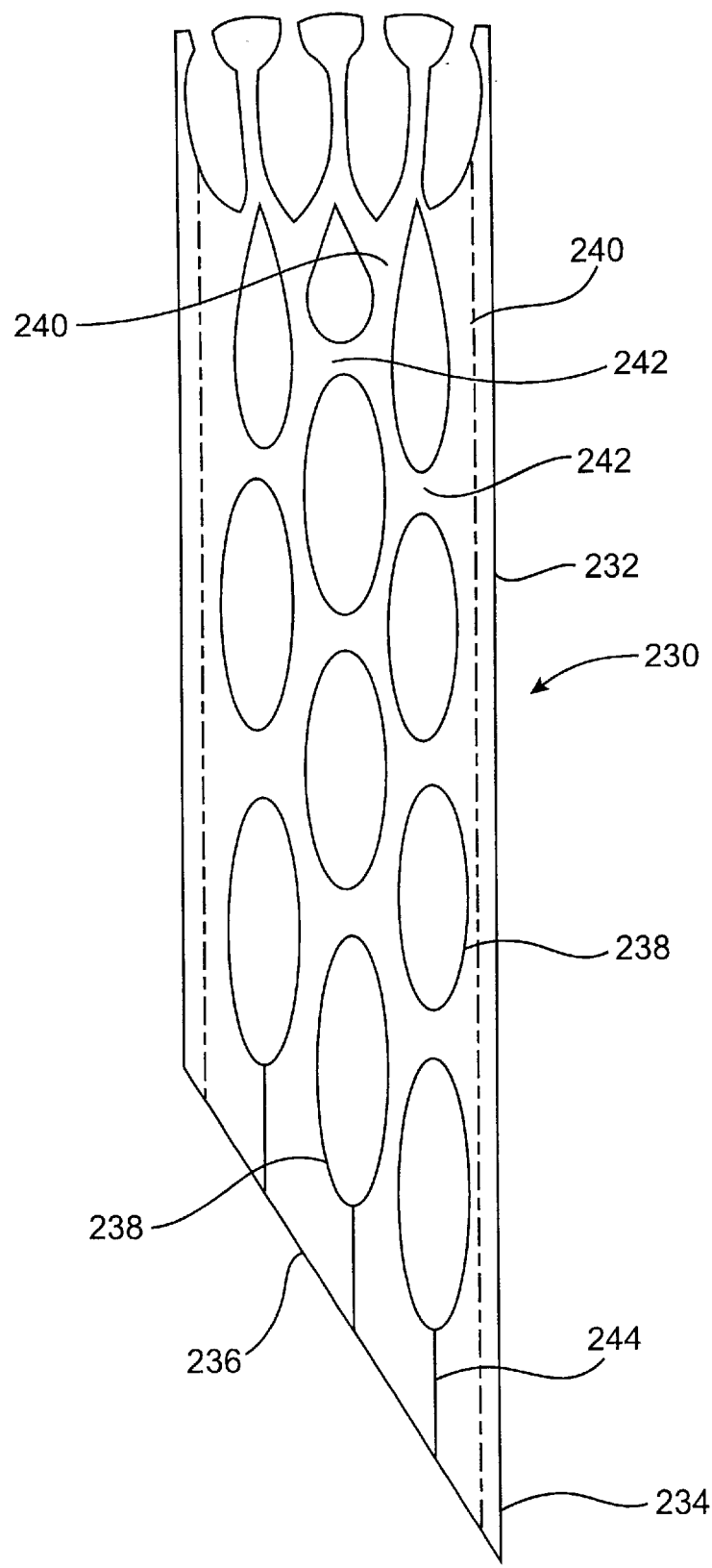
FIG. 18 is a side elevational view of a trocar according to a third alternative embodiment of the invention.

FIG. 18 shows a trocar 230 according to a third alternative embodiment. The trocar 230 includes a tubular member 232 with a piercing element 234, where the piercing element 234 is formed as an inclined surface 236 at a distal end of the tubular member 232. The tubular member 232 is formed as a deformable tubular wall, with a plurality of openings 238 along its surface. The openings 238 are defined by a plurality of axially extending wall sections 240 and a plurality of circumferentially extending wall sections 242. The openings 238 allow the tubular member 232 to be expanded over the holder tube which results in the tubular member 232 being deformed from a smaller configuration to a larger configuration. Preferably, the inclined surface 236 is a continuous surface interrupted by a plurality of slits 244 extending between the inclined surface 236 and the openings 238. The tubular member 232 may optionally include a tear line 246, which allows further expansion of the tubular member 232.

FIG. 19 shows a trocar 250 according to a fourth alternative embodiment. The trocar 250 includes a first and second trocar portion 251 and 253, respectively. The first trocar portion 251 includes a piercing element 252 in the shape of a cone with a vessel wall piercing portion 254 and a trimming portion 256. The first trocar portion 251 includes one or more axial slots 255 which allow the trocar portion 251 to be radially expanded during delivery of the anastomosis device through the interior of the trocar 250. The second trocar portion 253 is a tubular member which also includes one or more axial slots 258 for expansion of the second trocar portion 253 during delivery of the anastomosis device.

The piercing element 252 is inserted completely within the target vessel so that piercing portion 254 forms an incision in the target vessel wall, while the trimming portion 256 is also contained inside the target vessel. Once the incision is made, the trimming portion 256 is retracted from vessel wall so that tissue surrounding the incision is removed by a cutting action between the edge of the trimming portion 256 and the facing edge 257 of the second trocar portion 253.

FIG. 20 shows a trocar 260 according to a fifth alternative embodiment. The trocar 260 includes a piercing element 262 disposed at the distal end of a tubular member 264. The piercing element 262 includes a cutting blade 266 which forms an elongated slit upon insertion of the piercing element 262 into the vessel wall. Preferably, the cutting blade 266 includes two cutting edges 267 which meet at a point which form an angle therebetween. The cutting blade 266 can be flat or have a convex or concave shape (e.g., the blade 266 can have the curvature of the tubular member 264) and sized to provide the incision with a size smaller than the anastomosis device in an expanded condition. The tubular member 264 can also includes tines 268 at its distal end, which are separated by slits 270. Preferably, the distal ends of the tines 268 are biased towards each other at a location spaced from the distal end of the cutting blade 266, so that upon deployment of the anastomosis device, the incision formed in the target vessel wall is minimized.

FIGS. 21 and 22 show a trocar 280 according to a sixth alternative embodiment. The trocar 280 includes a tubular member 282 having a piercing element 284 at its distal end. The piercing element 284 includes a piercing portion 286 and a trimming portion 288. In this embodiment, the piercing portion 286 is comprised of a plurality of axially extending tines 290 at the distal end of the tubular member 282. The trimming portion 288 comprises cutting edges on outer surfaces of the tines 290.

The piercing element 284 is inserted completely within the target vessel so that piercing portion 286 forms an incision in the target vessel wall 32, while the trimming portion 288 is also contained inside the target vessel wall 32, as shown in FIG. 21. Once the incision 34 is made, the piercing element 284 and tubular member 282 are retracted away from the target vessel wall 32, causing the trimming portion 288 to cut away tissue surrounding the incision, as shown with reference to FIG. 22. The cut away tissue can be allowed to dangle on the outside of the target vessel. When the graft vessel is attached to the target vessel such tissue can be used to promote better growth of adjacent tissue between the surfaces of the graft vessel and target vessel.

Figure 23:
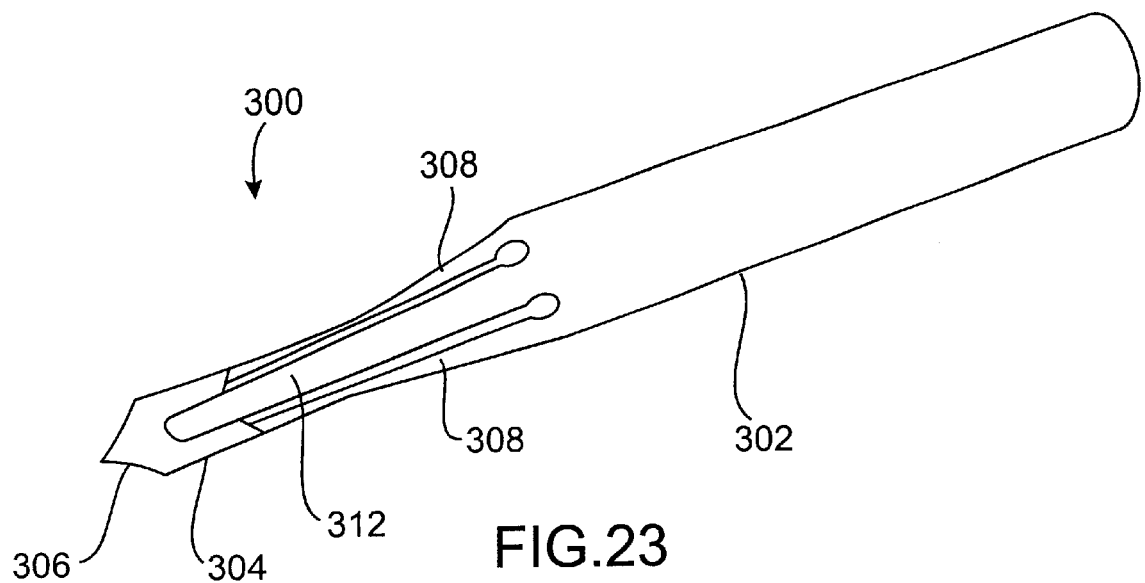
FIG. 23 is a perspective view of a trocar according to a seventh alternative embodiment of the invention.

FIG. 23 shows a trocar 300 according to a seventh alternative embodiment. The trocar 300 includes a tubular portion 302 with a piercing member 304 at its distal end. The piercing member 304 includes a cutting blade 306, which is shaped according to the cutting blade 266 of FIG. 20. In addition, the trocar 300 includes a plurality of tines 308 at its distal end, which are separated by slots 310. Preferably, the distal ends of the tines 308 are biased towards each other at a location spaced from the distal end of the cutting blade 306, so that upon deployment of the anastomosis device, the incision formed in the target vessel wall is minimized. In addition, the tubular member 302 may optionally include an additional tine 312, which is positioned between the tines 308, and opposite the cutting blade 306. According to this embodiment, the longer tine 312 can be used to prevent the shorter tines from impinging the target vessel wall opposite to the incision and thus avoid the potential for unwanted spreading of a puncture in the opposite wall during delivery of the anastomosis device.

Figure 24:
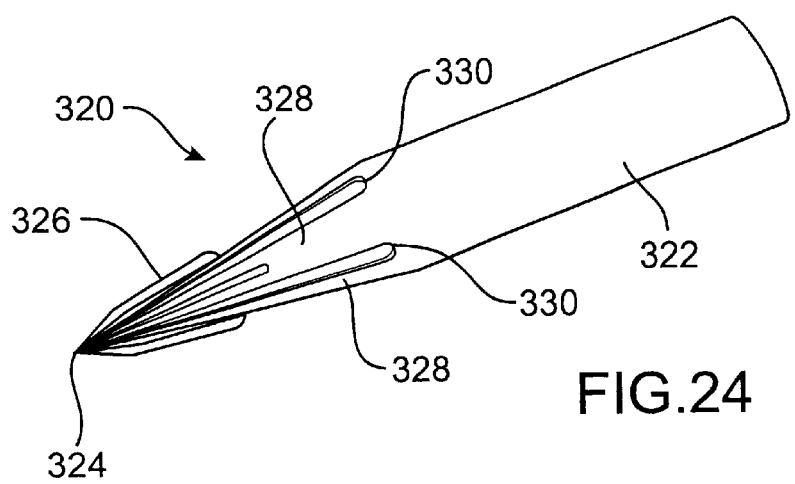
FIG. 24 is a perspective view of a trocar according to an eighth alternative embodiment of the invention.

FIG. 24 shows a trocar 320 according to an eighth embodiment. The trocar 320 includes a tubular portion 322 with a piercing member 324 at its distal end. The piercing member 324 includes a plurality of cutting blades 326, e.g. four cutting blades oriented at 90° to each other. The trocar 320 includes a plurality of elastically deformable tines 328 separated by axially extending slots 330. Preferably, the distal ends of the tines are biased towards each other during formation of an incision but bend outwardly over the deployment tool when the trocar is withdrawn from the target vessel. The blades 326 are intended to make small slits around the edge of the incision in order to relieve stress in the tissue and thus avoid a large tear from propagating along the target vessel. In the case of an aorta, collagen is oriented circumferentially and punctures of the aorta wall can lead to larger tears than desired when the incision opening is stretched (e.g., during expansion of the anastomosis device or the trocar). By providing small cuts around the incision it is possible to minimize such tearing.

Figure 25:
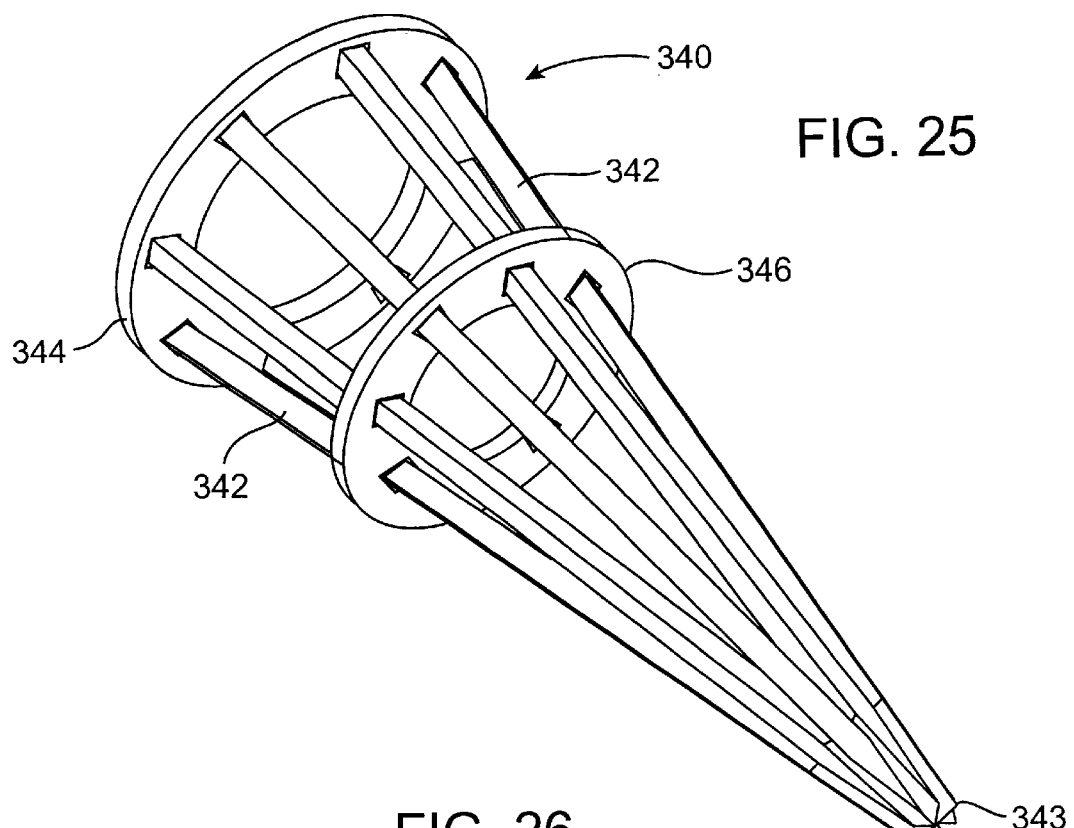
FIGS. 25 and 26 are perspective views of a trocar according to a ninth alternative embodiment of the invention.
Figure 26:
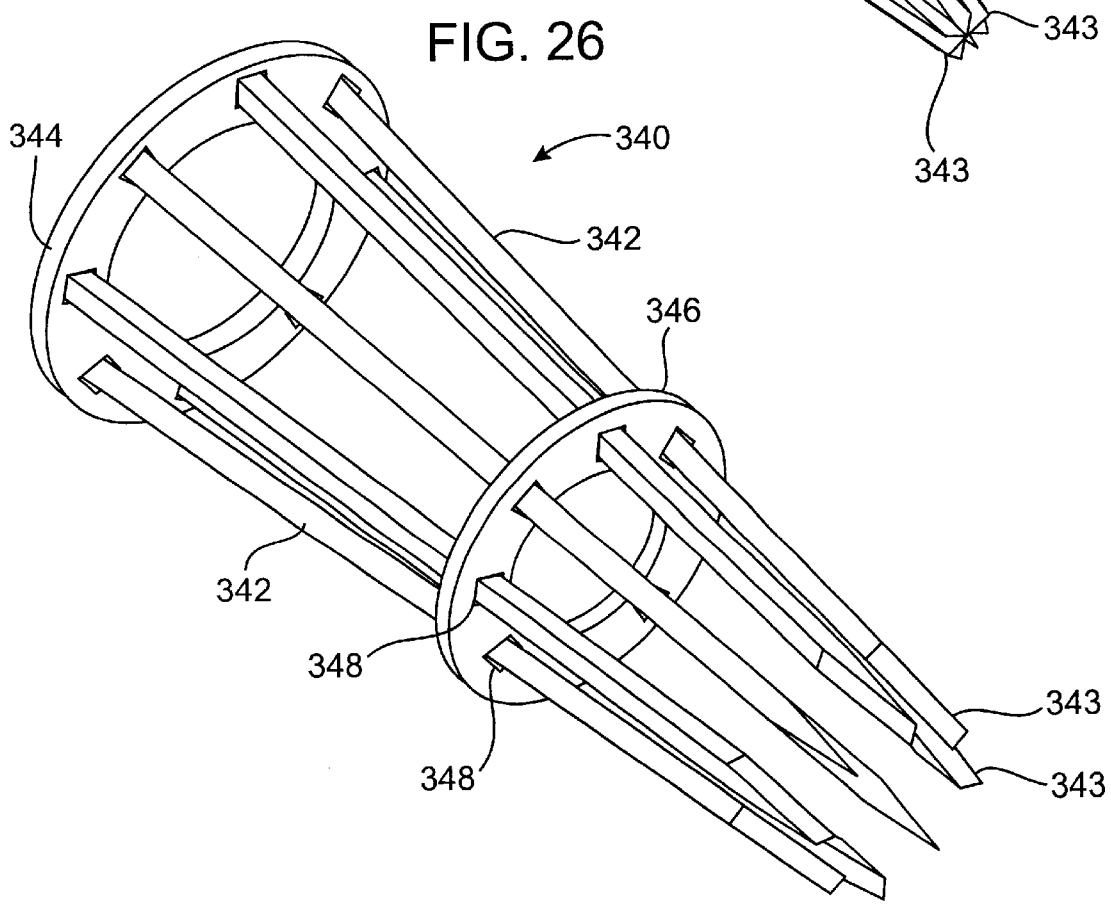

FIGS. 25 and 26 show an embodiment of a trocar 340 according to a ninth embodiment of the invention. The trocar 340 includes a plurality of axial members 342 and circumferential frame members 344, 346. The frame member 346 is movable along the axial members 342 which pass through openings 348 in the frame member 346 whereby the axial members 342 can be moved. For example, the frame member 346 can be moved from a first retracted position at which the tips 343 of the axial members 342 are brought together (FIG. 25) for forming an incision to a second position at which the tips 343 are spread apart for spreading the incision to allow introduction of the anastomosis device into the incision. The frame member 346 can be moved by any suitable arrangement such as a control rod or rods for opening and closing the tips of the axial members.

According to another aspect of the invention, the trocar assembly can be designed so as to punch out a section of the target vessel when the incision is formed. For example, the trocar can include a piercing element which forms an incision upon striking the target vessel wall and removes tissue surrounding the incision by compressing the tissue between the piercing element and another element such as an introducer tube which surrounds the piercing element. The piercing element can include a tapered tip for punching through the target vessel wall to form the incision and an anvil surface for enlarging the incision formed by the tapered tip by trapping tissue between the anvil surface and a surface of the introducer tube. The anvil surface can have any desired shape such as a flat, curved or conical surface which may or may not form an angle such as a right angle, obtuse angle or acute angle with a central axis of the piercing element. Thus, while the illustrated embodiment has a perpendicular anvil surface, the anvil surface could be a conical surface or a flat surface which is skewed (i.e., non-perpendicular) to the central axis. With such a tool, after the piercing element forms the incision, the anvil surface can be used to contact the inner surface of the target vessel as the introducer tube is pressed against the anvil surface to cut the tissue surrounding the incision. In the case where the anvil surface is at an acute angle (e.g., 30 to 60°) the tissue removed by trapping the tissue between the anvil surface and the introducer tube can be retained in an annular space between the anvil surface and a reduced diameter portion (e.g., a shaft) of the piercing element extending from the anvil surface in a direction opposite to the tapered tip. By cutting the target vessel tissue in this manner (e.g., providing a rounded rather than slit type of incision), there is less tendency for the incision to tear when expanded by the deployment tool and/or expansion of the anastomosis device.

Figure 27:
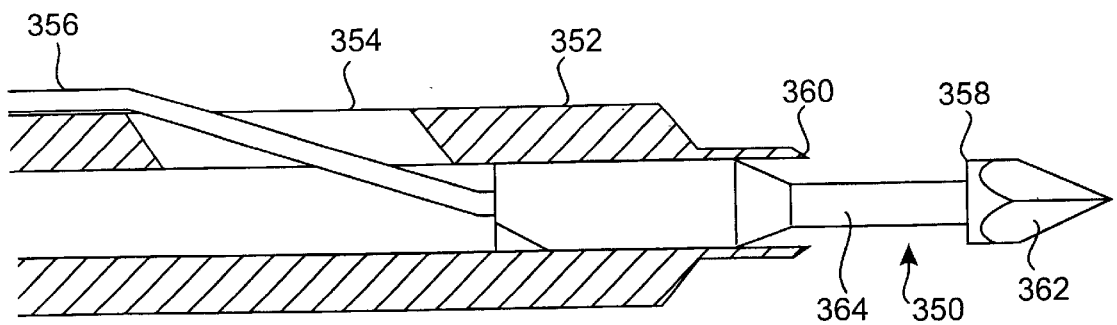
FIG. 27 is a perspective view of a trocar arrangement according to a tenth alternative embodiment of the invention wherein a one-piece piercing element can be retracted through an opening in a side of an introducer sheath.

FIG. 27 is a perspective view of a trocar arrangement according to a tenth alternative embodiment of the invention wherein a one-piece piercing element 350 can be supported and retracted by an elongated member 356 such as a steel strip or cable through an opening 352 in a side of an introducer sheath 354. The piercing element 350 forms an incision upon striking the target vessel wall and removes tissue surrounding the incision by compressing the tissue between an anvil surface 358 and an edge 360 of the introducer tube 352 which surrounds the piercing element 350. The piercing element 350 includes a tapered tip 362 formed, for example, by four ground surfaces extending from the anvil surface 358 which can have any desired configuration. With such a tool, after the tapered tip 362 forms the incision, the anvil surface 358 can be used to contact the inner surface of the target vessel as the edge 360 of the introducer tube 352 is pressed against the anvil surface 358 to cut the tissue surrounding the incision. The cut tissue can be trapped in an annular space surrounding the shaft 364. By cutting the target vessel tissue in this manner, there is less tendency for tearing the opening formed by the punched-out tissue when an anastomosis device is inserted into the opening or when the opening is expanded by expansion of the anastomosis device.

Figure 28:
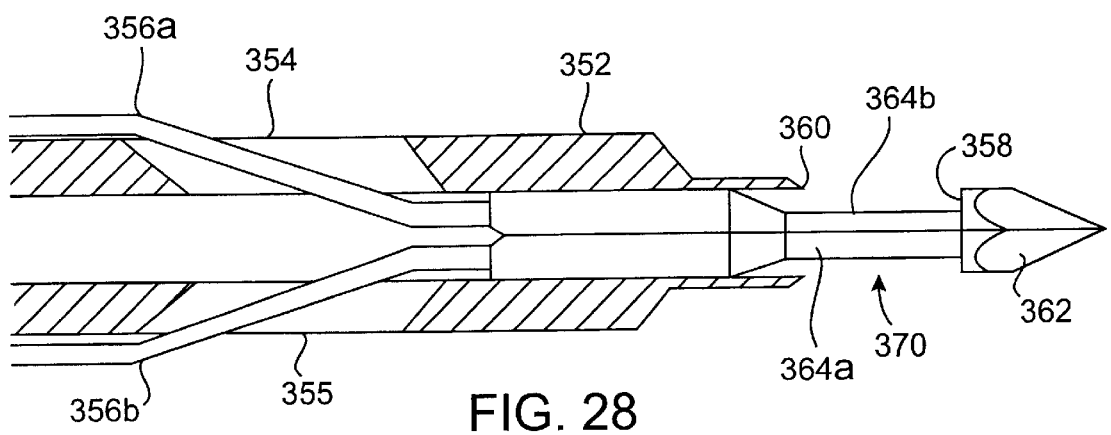
FIG. 28 is a perspective view of a trocar arrangement according to an eleventh alternative embodiment of the invention wherein segments of a multi-piece piercing element can be retracted through openings in a side of an introducer sheath.
Figure 29:
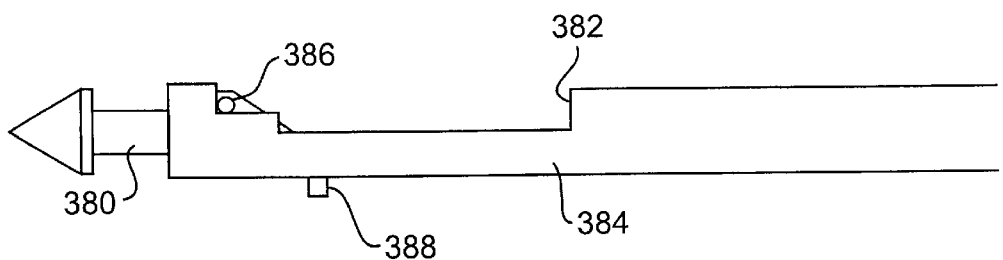
FIGS. 29–34 are perspective views of a trocar according to a twelfth alternative embodiment of the invention wherein a one-piece piercing element can be pivoted as it is retracted through an opening in an introducer sheath, FIG. 29 showing partial retraction, FIG. 31 showing initial pivoting, FIG. 32 showing further pivoting, FIG. 33 showing further retraction after completion of pivoting, and FIG. 34 showing completion of retraction.
Figure 30:
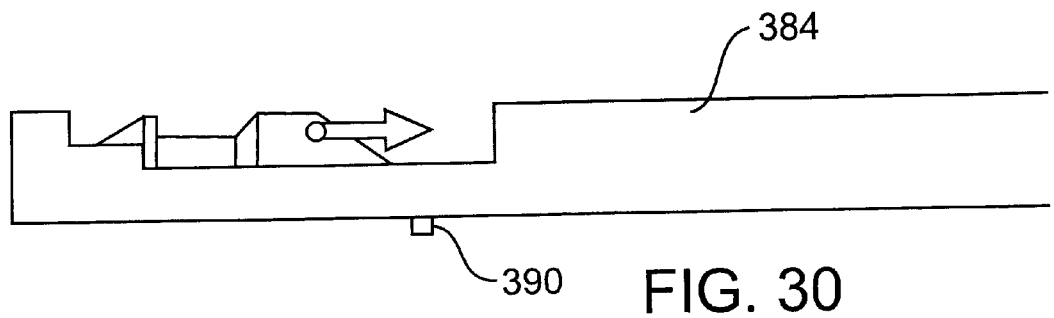

FIG. 28 is a perspective view of a trocar arrangement according to an eleventh alternative embodiment of the invention wherein segments of a multipiece piercing element 370 can be supported and retracted by elongated elements such as steel strips or cables 356a, 356b through openings 354 and 355 in a side of an introducer sheath 352. Like the piercing element 350, the piercing element 370 forms an incision upon striking the target vessel wall and removes tissue surrounding the incision by compressing the tissue between an anvil surface 358 and an edge 360 of the introducer tube 352 which surrounds the piercing element 370. The piercing element 370 is bifurcated along the central axis thereof and includes a tapered tip 362 formed, for example, by four ground surfaces extending from the anvil surface 358 which can have any desider configuration. With such a tool, after the tapered tip 362 forms the incision, the anvil surface 358 can be used to contact the inner surface of the target vessel as the edge 360 of the introducer tube 352 is pressed against the anvil surface 358 to cut the tissue surrounding the incision. If desired, however, only one of the piercing element halves can be slid forward to form a smaller incision and the other piercing element half can then be slid into the target vessel until the piercing element halves line up to form the anvil surface. The cut tissue can be trapped in an annular space around the shaft halves 364a, 364b. Upon retraction of the shaft halves 364a, 364b through the openings 354, 355 the ring of removed tissue may remain on one of the shafts or it can be removed by the surgeon using forcepts or other suitable tool. By cutting the target vessel tissue in this manner, there is less tendency for tearing the opening formed by the punched-out tissue when an anastomosis device is inserted into the opening or when the opening is expanded by expansion of the anastomosis device.

Figure 31:
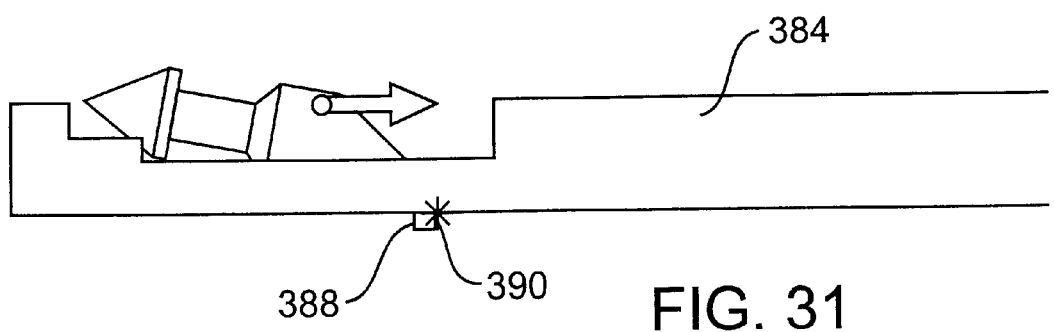
Figure 32:
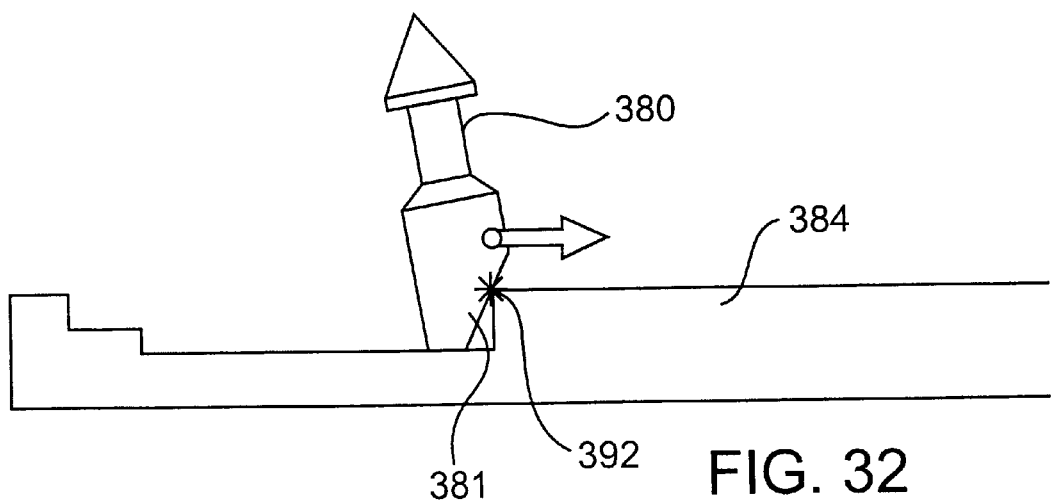
Figure 33:
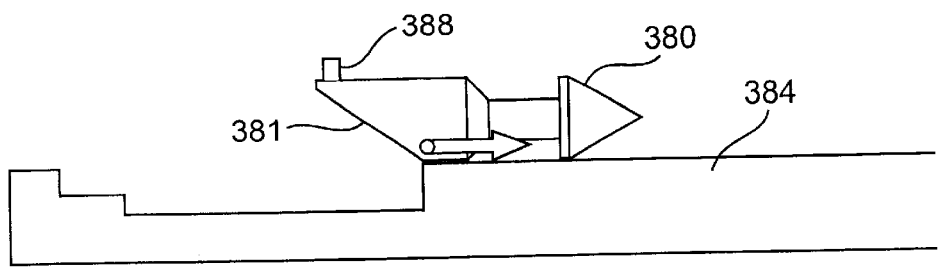
Figure 34:
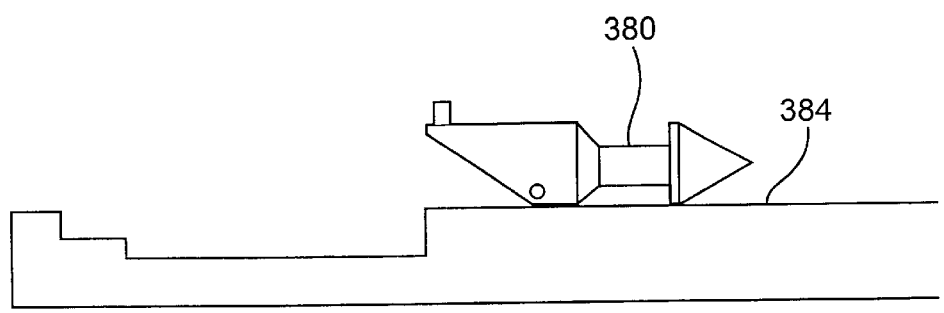

FIGS. 29–34 are perspective views of a trocar according to a twelfth alternative embodiment of the invention wherein a one-piece piercing element 380 can be pivoted as it is retracted through an opening 382 in an introducer sheath 384. As shown, the piercing element 380 includes side pins 386 which are retracted by pull wires or other arrangement (not shown) to accomplish punching of the tissue in the manner described above in connection with FIGS. 27–28. During such retraction, a pin 388 on the underside of the piercing element contacts a stop 390 (FIG. 30) at the end of a slot in the introducer tube 384 causing the piercing element 380 to pivot about the stop 390 (FIG. 31). Further retraction causes an inclined surface 381 of the piercing element to contact an edge 392 of the introducer tube such that the piercing element 380 rotates out of the opening 382 (FIG. 32) until the piercing element flips over (FIG. 33) and is pulled to a storage position outside the introducer tube (FIG. 34). When the piercing element is in the storage position, the inside of the introducer tube can be used for delivery of an anastomosis device to the incision in the target vessel.

Figure 35:
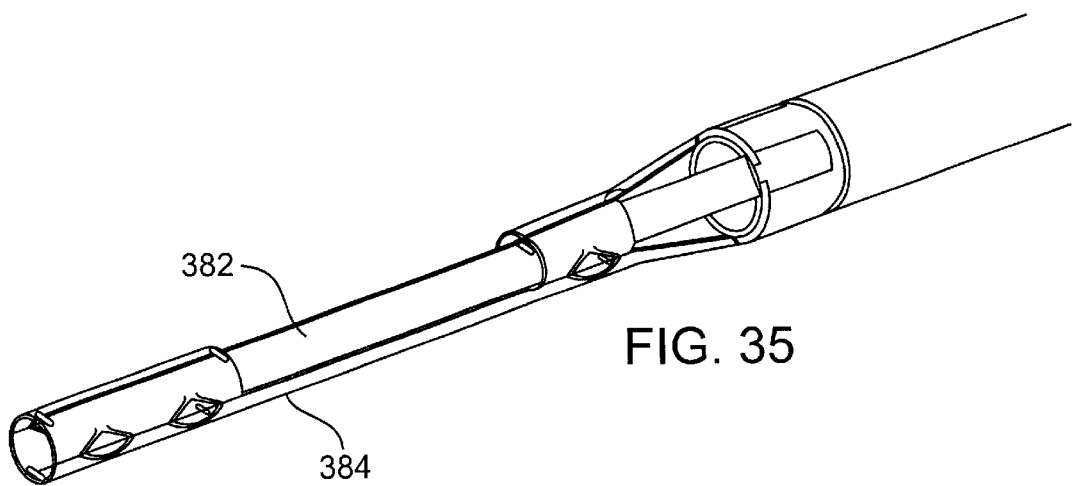
FIGS. 35–37 show details of an introducer tube which can be used with the embodiment shown in FIGS. 29–34.
Figure 36:
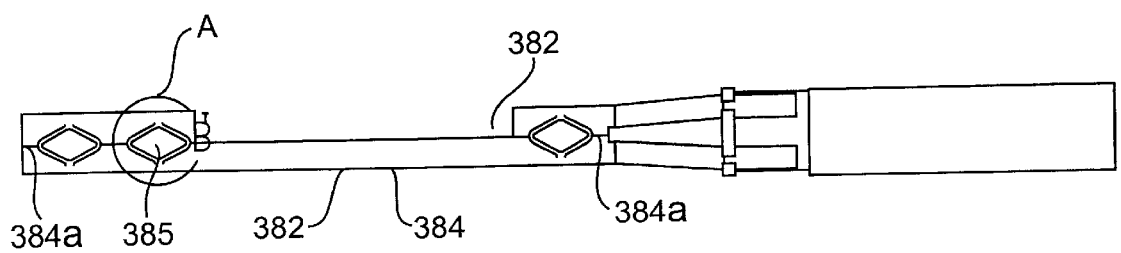
Figure 37:
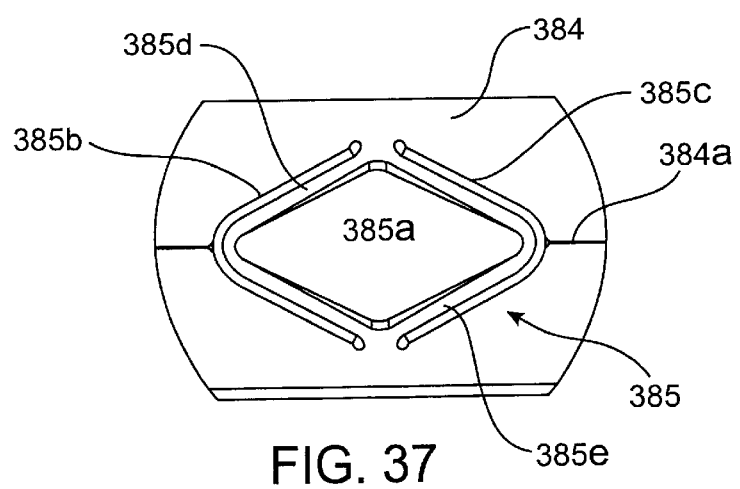

FIGS. 35–37 show details of an introducer tube which can be used with the embodiment shown in FIGS. 29–34. The introducer tube 384 is expandable over the deployment tool for delivering and deploying the anastomosis device. In order to allow such expansion, the tube 384 includes diametrically opposed cuts along lines 384a and includes expander sections 385. As shown in FIG. 37, which shows an enlarged view of detail A in FIG. 36, the expander section includes a plurality of cutouts 385a in the form of a rhombus and U-shaped cuts 385b, 385c which form strips 385d, 385e on opposite sides of each cutout 385a. The midpoints of the U-shaped cuts 385b, 385c are located along the cut 384a and the strips 385d, 385e are deformable to allow separation of the bifurcated tube 384.

Figure 38A:
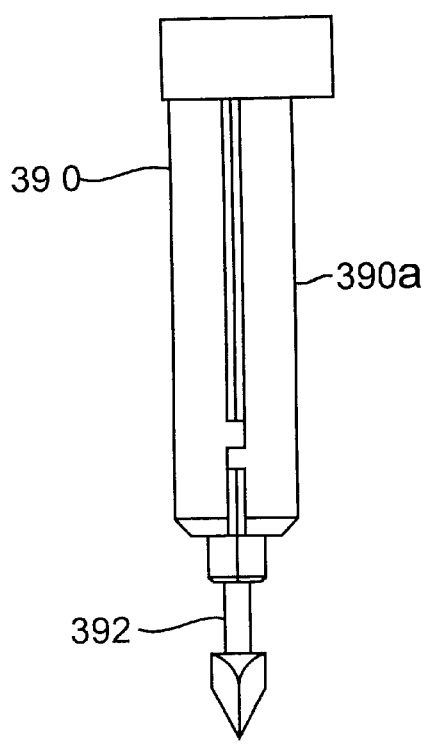
FIGS. 38A–C and 39A–C are perspective views of a trocar according to a thirteenth alternative embodiment of the invention wherein a one-piece piercing element can be supported and retracted by a flexible non-buckling element such as a steel strip to a storage position within an introducer sheath.
Figure 38B:
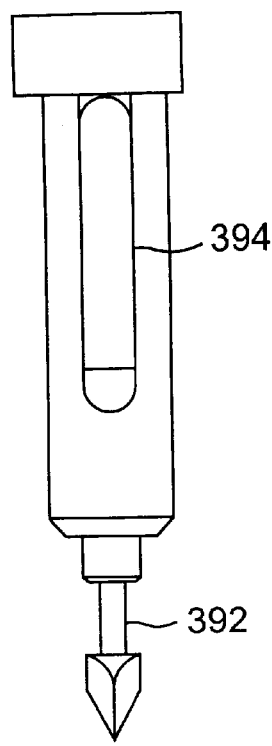
Figure 38C:
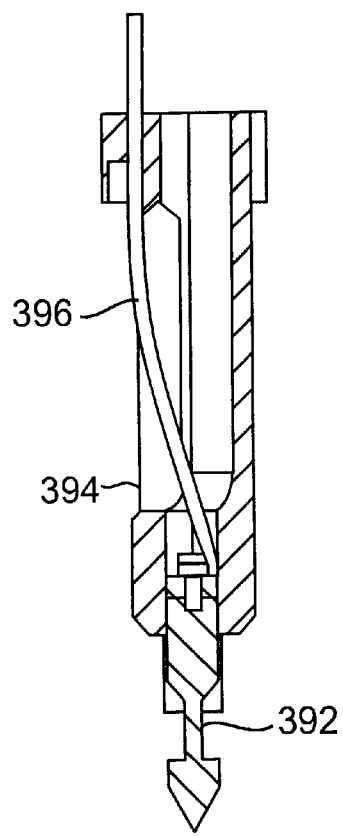
Figure 39A:
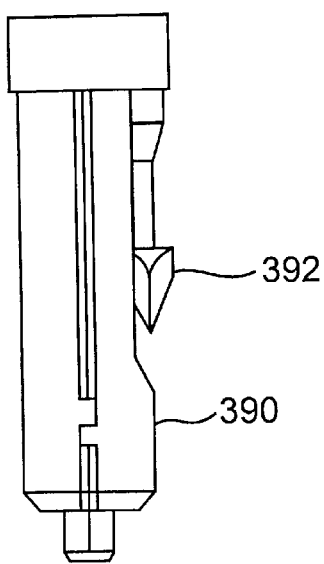
Figure 39B:
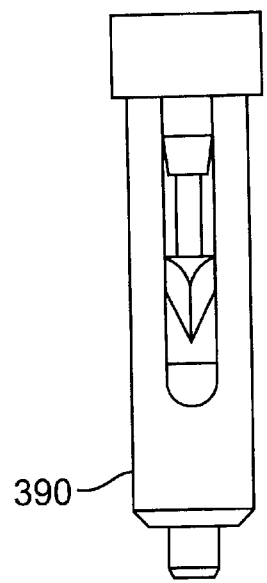
Figure 39C:
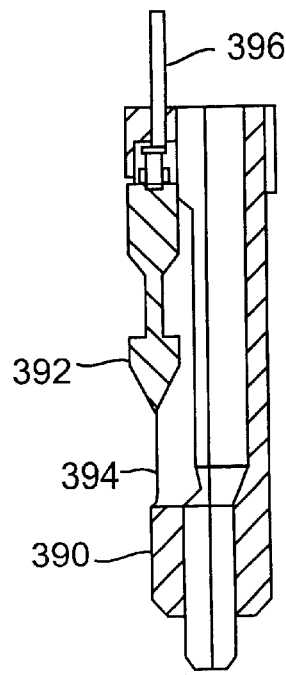
Figure 41A:
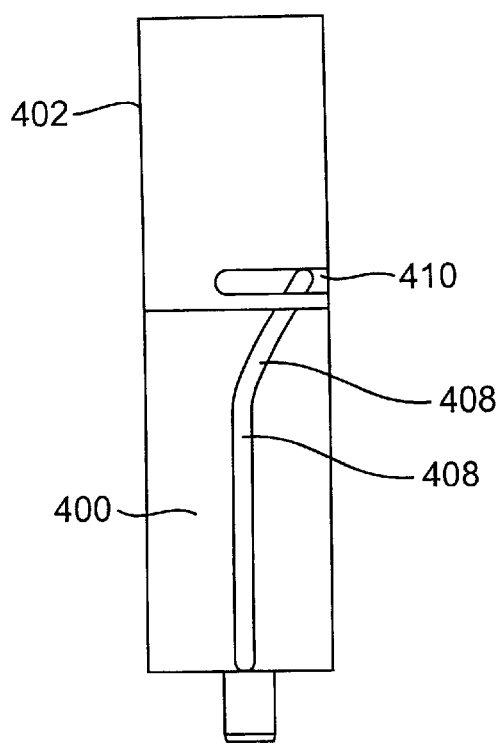
Figure 41B:
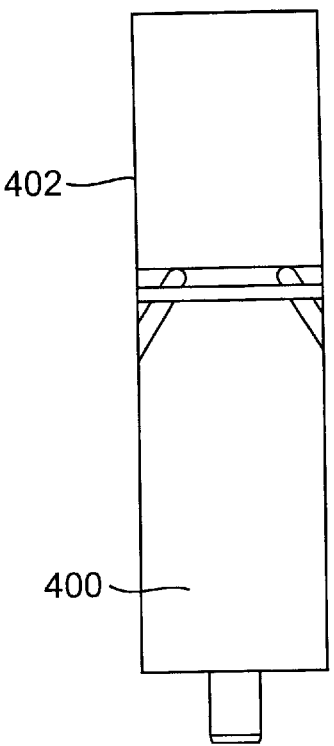
Figure 41C:
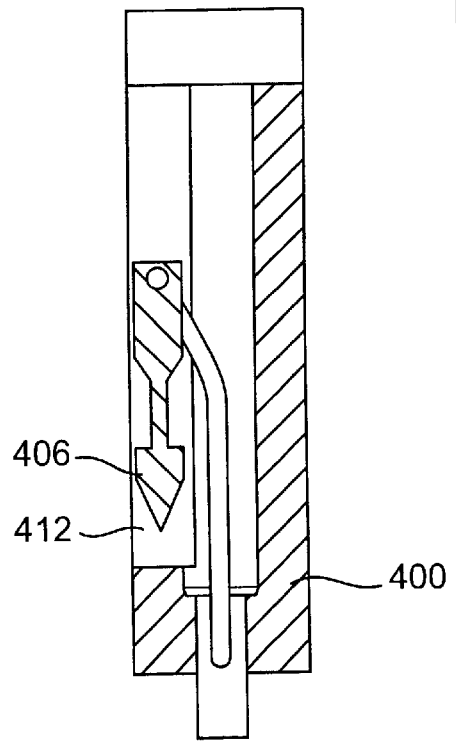

FIGS. 38A–C and 39A–C are perspective views of a trocar according to a thirteenth alternative embodiment of the invention wherein a one-piece piercing element can be retracted by a spring steel strap to a storage position within an introducer sheath. As shown in FIG. 38A, the tube 390 is bifurcated along cuts 390a, a piercing element extends out of one end of the tube and an elongated opening 394 (FIG. 38B) is located on one side of the tube between the cuts 390a. As shown in FIG. 38C, the piercing element 392 can be retracted into the tube by a member such as spring steel strap or cable 396 which extends out of the opening 394. The piercing element 392 is slidable in a bore in the tube from an incision forming position outside the tube to a storage position outside the opening, as shown in FIGS. 39A–C, wherein FIG. 39A is a side view, FIG. 39B is a front view and FIG. 39C is a sectional view through the axis of FIG. 39B. With this arrangement, the strap 396 prevents the piercing element from being retracted when it is pierced through the target vessel (e.g., aorta wall) and the piercing element 392 can then be pulled to the storage position by pulling back on the strap 396. With the piercing element thus pulled out of the opening 394, an anastomosis device can be delivered through the bore in the tube to the incision site. Because the two halves of the tube can be separated to allow radial expansion of the tube, the anastomosis device and the tool for delivering the device can be larger than the bore in the tube. FIGS. 40A–C and 41A–C are perspective views of a trocar according to a fourteenth alternative embodiment of the invention wherein a one-piece piercing element can be retracted by a pin and slot arrangement to a storage position within an introducer sheath. As shown in FIG. 40A, the insertion tube 400 includes a retraction tube 402 which is slidable along the outside of the tube 400 to cause pins 404 on the piercing element 406 to travel along slots 408 in the tube 400. The pins 404 on the piercing element 406 also extend through a circumferentially extending slot 410 in the outer tube 402 whereby the piercing element can be retracted into an opening 412 until it is held against the retraction tube 402. As the retraction tube 402 is retracted, the piercing element can be moved from an incision forming position outside the end of the tube 400 to a storage position within the opening 412, as shown in FIGS. 41A–C wherein FIG. 41A is a side view, FIG. 41B is a front view and FIG. 41C is a sectional view through the axis of FIG. 41B. With the piercing element thus pulled out of the central bore in the tube 400 and into the opening 412, an anastomosis device can be delivered through the bore in the tube to the incision site.

The trocars and anastomosis devices described above can be single piece or multi-piece devices which are formed by laser cutting or punching from a tube or sheet of material. The devices may be provided in varying sizes to join vessels of different sizes.

Although the invention has been principally discussed with respect to coronary bypass surgery, the trocar and/or anastomosis devices of the present invention may be used in other types of anastomosis procedures. For example, the trocar and/or anastomosis device may be used in femoral-femoral bypass, vascular shunts, subclavian-carotid bypass, organ transplants, and the like.

The trocar and/or anastomosis devices may be made of any known material which can be elastically or plastically deformed such as stainless steel, nickel titanium alloys, polymer materials, and the like.

While the invention has been described in detail with reference to the preferred embodiments thereof, it will be apparent to one skilled in the art that various changes and modifications can be made and equivalents employed, without departing from the present invention.

What is claimed is:

1. A device for forming an incision in a wall of a target vessel and delivering an anastomosis device for connecting an end of a graft vessel to a target vessel at the site of the incision, the device comprising:
   a member having a piercing element at a distal end thereof and the member being adapted to cooperate with a deployment tool such that the anastomosis device can be delivered to the incision site by the development tool and the piercing element can be withdrawn from the incision site prior to deployment of the anastomosis device, wherein the piercing element includes a cutting blade which is movable with respect to the member such that the cutting blade can be moved from a cutting position at which the cutting blade is exposed with respect to the member to a retracted position at which the cutting blade is not exposed with respect to the member.

2. The device of claim 1, wherein the piercing element comprises a sharpened inclined surface at the distal end of the member.

3. The device of claim 1, wherein the tubular member includes distal and proximal portions, the distal portion having a smaller diameter than the proximal portion, and the piercing element comprises a sharpened inclined surface being on a free end of the distal portion.

4. The device of claim 3, wherein the distal portion includes at least one axially extending tear line which allows the distal portion to be split and expanded over the deployment tool.

5. The device of claim 1, wherein the piercing element comprises a cutting blade which forms an elongated slit upon insertion of the piercing element into the vessel wall.

6. The device trocar of claim 3, wherein the piercing element comprises a tapered tip and anvil surface which forms a rounded incision upon insertion of the piercing element into the vessel wall.

7. A device for forming an incision in a wall of a target vessel and delivering an anastomosis device for connecting an end of a graft vessel to a target vessel at the site of the incision, the device comprising:
   a member having a piercing element at a distal end thereof and the member being adapted to cooperate with a deployment tool such that the anastomosis device can be delivered to the incision site by the deployment tool and the piercing element can be withdrawn from the incision site prior to deployment of the anastomosis device, wherein the member comprises a tubular member having a passage therein through which the anastomosis device is delivered to the incision site, and wherein the tubular member further includes a deformable tubular wall.

8. The device of claim 7, wherein the tubular wall includes openings therein which allow the tubular member to be deformed from a smaller configuration to a larger configuration.

9. The device of claim 8, wherein the openings are defined by a plurality of axially extending wall sections and a plurality of circumferentially extending wall sections.

10. The device of claim 8, wherein the inclined surface is a continuous surface interrupted by a plurality of slits extending between the inclined surface and the openings located closest to the inclined surface.

11. The device of claim 9, wherein the openings comprise axially extending slots arranged in a staggered pattern such that the circumferentially extending wall sections intersect a pair of the slots.

12. The device of claim 7, wherein the deformable tubular wall is made from plastic or metal.

13. A device for forming an incision in a wall of a target vessel and delivering an anastomosis device for connecting an end of a graft vessel to a target vessel at the site of the incision, the device comprising:

a member having a piercing element at a distal end thereof and the member being adapted to cooperate with a deployment tool such that the anastomosis device can be delivered to the incision site by the deployment tool and the piercing element can be withdrawn from the incision site prior to deployment of the anastomosis device, wherein the piercing element includes a cutting blade which is movable with respect to the member such that the cutting blade can be moved from a cutting position at which the cutting blade is exposed with respect to the member to a retracted position at which the cutting blade is not exposed with respect to the member, wherein the piercing element includes a vessel wall piercing portion and a trimming portion, the piercing portion forming the incision upon insertion of the distal end of the member into the vessel wall and the trimming portion removing tissue around the incision upon retraction of the member.

14. The device of claim 13, wherein the member comprises a tubular member and the piercing portion comprises a plurality of axially extending tines at the distal end of the tubular member.

15. The device of claim 13, wherein the piercing portion comprises a plurality of axially extending tines and the trimming portion comprises cutting edges on outer surfaces of the tines or the piercing portion comprises a tapered tip and the trimming portion comprises an anvil surface at one end of the tapered tip.

16. The device of claim 14, wherein distal ends of the tines are biased in close proximity to each other such that the incision can be formed by advancing the tines into the vessel wall, the incision being expanded by spreading of the tines upon delivery of the anastomosis device.

17. A device for forming an incision in a wall of a target cessel and delivering an anastomosis device for connecting an end of a graft vessel to a target vessel at the site of the incision, the device comprising:

a member having a piercing element at a distal end thereof and the member being adapted to cooperate with a deployment tool such that the anastomosis device can be delivered to the incision site by the deployment tool and the piercing element can be withdrawn from the incision site prior to deployment of the anastomosis device, wherein the piercing element comprises a cutting blade which forms an elongated slit upon insertion of the piercing element into the vessel wall, and the member comprises a tubular member which includes tines at the distal end thereof, the tines being separated from each other and from the cutting blade by axially extending slits.

18. The device of claim 17, wherein distal ends of the tines are biased in close proximity to each other at a location spaced from the distal end of the cutting blade.

19. A method of performing anastomosis comprising:

using a device to form an incision in a wall of a target vessel, the device comprising: a member having a piercing element at a distal end thereof, the member adapted to cooperate with a deployment tool such that an anastomosis device can be delivered to an incision site;

inserting the anastomosis device with the deployment tool into the incision, the anastomosis device having an end of a graft vessel everted around a first portion of the anastomosis device; and manipulating the first portion of the anastomosis device with respect to a second portion of the anastomosis device to capture edges of the incision in the target vessel with the anastomosis device such that a fluid passage is established between the graft vessel and the target vessel.

20. The method of claim 19, wherein the target vessel is an aorta and the method is performed without clamping of the aorta.

21. The method of claim 19, wherein the end of the graft vessel and the edges of the incision in the target vessel are captured between the first portion and the second portion and the end of the graft vessel abuts an outside of the target vessel, the first portion comprising an inner flange formed by radial expansion of the anastomosis device and the second portion comprising an outer flange formed by axial compression of the anastomosis device.

22. The method of claim 19, wherein the anastomosis device is expandable from a first configuration to a larger second configuration, the method including expanding the anastomosis device with an expander to cause a portion of the anastomosis device to extend outward forming the first flange, the first flange holding a portion of the graft vessel in contact with an inner surface of the target vessel.

23. The method of claim 22, further comprising retracting the device over the anastomosis device and along the expander prior to expanding the anastomosis device with the expander, the device being deformed during the retracting step.

24. The method of claim 23, wherein the second portion of the anastomosis device is formed by axially compressing the anastomosis device with a deployment tool.

25. The method of claim 24, wherein the deployment tool comprises a tube which engages a proximal end of the anastomosis device, the compressing step being carried out by moving the expander relative to the tube.

26. The method of claim 25, wherein a groove on the expander engages the anastomosis device during formation of the second portion.

27. The method of claim 19, wherein the piercing element includes a plurality of cutting edges which form small slits around the incision or the piercing element includes a tapered tip which forms the incision and an anvil surface which enlarges and rounds the incision.

28. The method of claim 19, wherein the anastomosis device comprises an expandable linkage which is delivered through the device to the site of the incision, the linkage being deformed to an expanded size during formation of the first and second portions, the incision formed by the device being smaller than the expanded size.

29. The method of claim 19, wherein the first and second portions form an angle between about 40 and 140 degrees with an axis of the anastomosis device.

* * * * *

UNITED STATES PATENT AND TRADEMARK OFFICE
CERTIFICATE OF CORRECTION

PATENT NO.     : 6,371,964 B1                                            Page 1 of 1
DATED          : April 16, 2002
INVENTOR(S)    : Vargas, Jaime et al.

It is certified that error appears in the above-identified patent and that said Letters Patent is hereby corrected as shown below:

Column 1,
Line 11, "per" should read -- performing --.

Column 4,
Line 45, "FIG. 22 showing" should read -- FIG. 21 showing --.

Column 14,
Line 20, "desider" should read -- desired --.
Line 34, "forcepts" should read -- forceps --.

Column 16,
Line 16, "development" should read -- deployment --.

Signed and Sealed this

Fourteenth Day of January, 2003

JAMES E. ROGAN
*Director of the United States Patent and Trademark Office*